United States Patent [19]

Warrellow et al.

[11] Patent Number: 5,786,354

[45] Date of Patent: Jul. 28, 1998

[54] TRI-SUBSTITUTED PHENYL DERIVATIVES AND PROCESSES FOR THEIR PREPARATION

[75] Inventors: Graham John Warrellow, Northwood; Rikki Peter Alexander, High Wycombe, both of United Kingdom

[73] Assignee: Celltech Therapeutics, Limited, Slough, United Kingdom

[21] Appl. No.: 492,639

[22] Filed: Jun. 20, 1995

[30] Foreign Application Priority Data

| Jun. 21, 1994 | [GB] | United Kingdom | 9412385 |
| Jun. 22, 1994 | [GB] | United Kingdom | 9412492 |

[51] Int. Cl.$^6$ .......................... A61K 31/435; A61K 31/44
[52] U.S. Cl. .................... 514/277; 514/357; 546/329; 546/339
[58] Field of Search .................... 514/277, 357; 546/339, 340, 329, 343, 344

[56] References Cited

U.S. PATENT DOCUMENTS

| 4,012,495 | 3/1977 | Schmiechen et al. | 424/274 |
| 4,015,017 | 3/1977 | Gazave | 424/331 |
| 4,153,713 | 5/1979 | Huth et al. | 424/274 |
| 4,193,926 | 3/1980 | Schmiechen et al. | 260/326.5 |
| 4,303,649 | 12/1981 | Jones | 424/177 |
| 4,788,195 | 11/1988 | Torley et al. | 514/252 |
| 4,792,561 | 12/1988 | Walker et al. | 514/312 |
| 4,876,252 | 10/1989 | Torley et al. | 514/224.8 |
| 4,897,396 | 1/1990 | Hubele | 514/275 |
| 4,921,862 | 5/1990 | Walker et al. | 514/312 |
| 4,966,622 | 10/1990 | Rempfler et al. | 71/92 |
| 4,971,959 | 11/1990 | Hawkins | 514/150 |
| 5,124,455 | 6/1992 | Lombardo | 546/181 |
| 5,128,358 | 7/1992 | Saccomano et al. | 514/392 |
| 5,159,078 | 10/1992 | Rempfler et al. | 544/330 |
| 5,175,167 | 12/1992 | Zipperer et al. | 514/277 |
| 5,177,085 | 1/1993 | Naef | 514/307 |
| 5,236,918 | 8/1993 | Amschler et al. | 514/247 |
| 5,274,002 | 12/1993 | Hawkins | 514/530 |
| 5,298,511 | 3/1994 | Waterson | 514/311 |
| 5,326,898 | 7/1994 | Chandraratna | 560/17 |
| 5,340,827 | 8/1994 | Beeley et al. | 514/352 |
| 5,491,147 | 2/1996 | Boyd et al. | 514/247 |
| 5,550,137 | 8/1996 | Beeley et al. | 514/354 |
| 5,580,888 | 12/1996 | Warrellow et al. | 514/332 |
| 5,608,070 | 3/1997 | Alexander et al. | 546/270 |
| 5,693,659 | 12/1997 | Head et al. | 514/357 |

FOREIGN PATENT DOCUMENTS

| 0 233 461 A2 | 8/1987 | European Pat. Off. . |
| 0 295 210 A1 | 12/1988 | European Pat. Off. . |
| 0 337 943 A2 | 10/1989 | European Pat. Off. . |
| 0 393 500 | 10/1990 | European Pat. Off. . |
| 0 490 823 | 6/1991 | European Pat. Off. . |
| 0 470 805 | 2/1992 | European Pat. Off. . |
| 0497564A1 | 8/1992 | European Pat. Off. . |
| 0 511 865 | 11/1992 | European Pat. Off. . |
| 0 537 742 | 4/1993 | European Pat. Off. . |
| 0 564 409 A1 | 10/1993 | European Pat. Off. . |
| 2 545 356 A1 | 11/1994 | France . |
| 250 1443 | 7/1975 | Germany . |
| 3-77872 | 4/1991 | Japan . |
| 3-77923 | 4/1991 | Japan . |
| 1588639 | 4/1981 | United Kingdom . |
| WO 87/06576 | 11/1987 | WIPO . |
| WO 91/15451 | 10/1991 | WIPO . |
| WO 91/16892 | 11/1991 | WIPO . |
| WO 92/00968 | 1/1992 | WIPO . |
| WO 92/06085 | 4/1992 | WIPO . |
| WO 92/06963 | 4/1992 | WIPO . |
| WO 92/07567 | 5/1992 | WIPO . |
| WO 92/12961 | 8/1992 | WIPO . |
| WO 92/19594 | 11/1992 | WIPO . |
| WO 92/19602 | 11/1992 | WIPO . |
| WO 93/10118 | 5/1993 | WIPO . |
| WO 93/19748 | 10/1993 | WIPO . |
| WO 94/02465 | 2/1994 | WIPO . |

(List continued on next page.)

OTHER PUBLICATIONS

Chan, A.C. et al., "The Role of Protein Tyrosine Kinases and Protein Tyrosine Phosphatases in T Cell Antigen Receptor Signal Transduction", *Annu. Rev. Immunol.*, 1994, 12, 555–592.

Daves, G.D. et al., "Pyrimidines. XIII. 2–and 6–Substituted 4–Pyrimidinecarboxylic Acids", *J. of Hev. Chem.*, 1964, 1, 130–133.

Dietl, F. et al., "Chinone von Benzo–und Dibenzokronenethern", *Synthesis*, 1985, 626–631.

Geissler, J.F. et al., "Thiazolidine–Diones. Biochemical and Biological Activity of a Novel Class of Tyrosine Protein Kinase Inhibitors", *J. of Biol. Chem.*, 1990, 265(36), 22255–22261.

(List continued on next page.)

*Primary Examiner*—Amelia Owens
*Attorney, Agent, or Firm*—Woodcock Washburn Kurtz Mackiewicz & Norris LLP

[57] ABSTRACT

Tri-substituted phenyl derivatives and processes for their preparation. In a preferred embodiment, the compounds have the general formula (2)

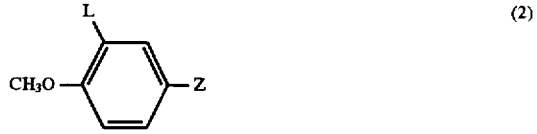

(2)

wherein L is preferably —OR; Z is preferably —C(R$^3$)(R$^4$) —C(R$^5$)(R$^6$)(R$^7$); R is preferably an optionally substituted cycloalkyl group: R$^3$ is preferably hydrogen; R$^4$ is hydrogen, —(CH$_2$)$_r$Ar or —(CH$_2$)$_r$—Ar—(L$^1$)$_n$—Ar'; R$^5$ is —(CH$_2$)$_r$Ar or —(CH$_2$)$_r$—Ar—(L$^1$)$_n$—Ar'; R$^6$ and R$^7$ are preferably hydrogen or methyl; Ar is a monocyclic or bicyclic aryl or heteroaryl group; L$^1$ is a divalent linking group; and Ar' is Ar or an Ar containing group. Compounds of the invention are potent and selective phosphodiesterase type IV inhibitors and are useful in the prophylaxis and treatment of various diseases, such as asthma, which are associated with an unwanted inflammatory response or muscular spasm.

21 Claims, No Drawings

FOREIGN PATENT DOCUMENTS

| | | |
|---|---|---|
| WO 94/10118 | 5/1994 | WIPO. |
| WO 94/12461 | 6/1994 | WIPO. |
| WO 94/14742 | 7/1994 | WIPO. |
| WO 95/09847 | 4/1995 | WIPO. |
| WO 95/09851 | 4/1995 | WIPO. |
| WO 95/09852 | 4/1995 | WIPO. |
| WO 95/09853 | 4/1995 | WIPO. |
| WO 95/17386 | 6/1995 | WIPO. |

OTHER PUBLICATIONS

Hanks, S.K. et al., "The eukaryotic protein kinase superfamily: kinase (catalytic) domain strucutre and classification", FASEB J., 1995, 9, 576–596.

Iwashita, S. et al., "Signal Transduction System for Growth Factor Receptors Associated with Tyrosine Kinase Activity: Epidermal Growth Factor Receptor Singalling and Its Regulation", Cellular Signalling, 1992, 4(2), 123–132.

Newton, A.C., "Protein Kinase C: Structure, Function, Regulation", J. Biol. Chem., 1995, 270(48), 28495–28498.

Ohtani, Y. et al., "Studies on Pitch Problems Caused by Pulping and Bleaching of Tropical Woods. XIV. Chemistry of the Aurone Derivatives at the Conventional Bleaching Stages", Acta Chem. Scand., 1982, 613–621.

Pines, J., "Cyclins and cyclin–dependent kinases: take your partners", TIBS, 1993, 18, 1995–197.

Plé, N. et al., "Metalation of Diazines. XI. Directed Ortho–Lithiation of Fluoropyrimidines and Application to Synthesis of an Azacarboline", J. Heterocyclic Chem., 1994, 31, 1311–1315.

Sánchez, H.I. et al., "Formal Total Synthesis of β–Pipitzol", Tetrahedron, 1985, 41(12), 2355–2359.

Karlsson, J.-A., et al., T–Lymphocyte and Inflammatory Cell Research in Asthma, pp. 323–347 (1993), ed. Joller, G., et al., Academic Press.

Ashton, "Selective Type IV Phosphodiesterase Inhibitors as Antiasthmatic Agents. The Syntheses and Biological Activities of 3–(Cyclopentyloxy)–4–methyoxybenzamides and Analogues" J. Med. Chem. 37:1696–1703 (1994).

Beavo & Reifsnyder, "Primary Sequence of Cyclic Nucleotide Phosphodiesterase Isozymes and the Design of Selective Inhibitors" TIPS 11: 150–155 (1990).

Buu–Hoi, N.P. et al., "Bromination of Some 1,2,2–Triarylethylenes" J. of Organic Chemistry, 1261–1263 (Sep., 1958).

Buu–Hoi et al., "New Method for the Synthesis of ω,ω–Diarylacetophenones Aminated in the Aromatic Nucleus. Plynitration of Triarylethylenes" Chemical Abstracts 61:16006h (1964).

Chemical Abstracts. Registry Handbook—Number Section. Printed Issues Columbus US *compounds with registry numbers 95992–21–5; 95971–60–1; 90053–37–5; 82668–18–6; 80395–25–1; 49610–49–3 (1976).

El–Wakil et al., "Study of the proton magnetic resonance of methoxytamoxifen towards ortho–substitiution" Chemical Abstracts 116: 255248t (1992).

Hirose et al., "Styrene Derivatives and Electrophotpgraphic Photoreceptor Containing Them" Chemical Abstracts 118: 136183z (1993).

Lisle, H. et al., "IL–2–Induced Eosinophilia in the Rat Pleural Cavity: The Effect of Dexamethasone and Indomethacin", Br. J. Pharmacol. 1993, 108, 230.

Livi et al., "Cloning and Expression of cDNA for a Human Low–$K_m$3 Rolipram–sensitive Cyclic AMP Phosphodiesterase", Molecular and Cellular Biol. 1990, 10, 2678.

Ishikura, M. et al., "An Efficient Synthesis of 3–Heteroarylpyridines via Diethyl–(3–pyridyl)–borane" Synthesis pp. 936–938 (1984).

Manhas et al., "heterocyclic Compounds XII. Quinzoline Derivatives as Potential Antifertility Agents(1)" J. Heterocyclic Chem: 711–715 (1979).

Meyers, A.J. et al., "Oxazolines. XI. Synthesis of Functionalized Aromatic and Aliphatic Acids. A Useful Protecting Group for Carboxylic Acids Against Grignard and Hydride Reagents", J. Org. Chem. 1974, 39, 2787.

Mezheritskaya, "Synthesis and properties of carboxonium het=erocyclic systems. VII. Synthesis and properties of 2–benzyl–substituted 1,3–dioxolanium salts" Chem. Abs. 93: 95160j p. 635(1980).

Mitsunobu, O., "The Use of Diethyl Azodicarboxylate and Triphenylphosphine in Synthesis and Transformation of Natural Products" Synthesis 1–28 (1981).

Nicholson et al., "Differential Modulation of Tissue Function and Therapeutic Potential of Selective Inhibitors of Cyclic Nucleotide Phosphodiesterase Isoenzymes" TIPS 12: 19–27 (1991).

O'Connor et al., "Voltammetry and Controlled Potential Oxidation of 3,4–dimethoxypropenylbenzene at a rotating platinum electrode in unbuffed acetonitrile and in acetonitrile–pyridine solution" Chemical Abstracts 60(8) #10203.4 (Apr. 13, 1964).

Porter et al., "Preparation of 6–phenyl–3–(5–tetrazolyl)pyridin–=2(H)–one Derivatives as Cyclic AMP–dependent Protein Kinase Agonists" Chem. Abstract 117(9) : 90296n (1992).

Ramalingam, Deshmukh and Sattur, "Synthesis and Pharmacology of 2,5–Disubstituted 1,3,4–Zxadiazoles" J. Indian Chem. Soc. vol. 58(3) 269–271 (1981).

Reddy et al., "Inhibition of Breast Cancer Cell Growth in Vitro by a Tyrosine Kinase Inhibitor" Cancer Research 52: 3636–3641 (1992).

Schneider et al., "Catechol Estrogens of the 1,1, 2–Triphenylbut–1–ene Type: Relationship Between Structure, Estradiol Receptor Affinity, Estrogenic and Antiestrogenic Properties, and Mammary Tumor Inhibitng Activities" J. Med. Chem. 29: 1355–1362 (1986).

Seintz et al., "Fluorotamoxifen. A Cavevat on the Generality of Electrophilic Destannylation" Chemical Abstracts 111: 57133k (1989).

Sharp, M.J. et al., "Synthetic Connections to the Aromatic Directed Metalation Reaction. Functionalized Aryl Boronic Acids by Ipso Borodesilylation; General Synthesis of Unsymmetrical iphenyls and n–Terphenyls" Tetrahedron Lett 28: 5093–5096 (1987).

Thompson, W.J. and Gaudino, J., "A General Synthesis of 5–Arylnicotinates" J. Org. Chem. 49: 5237–5243 (1984).

Yeadon et al., "Mechanisms Contributing to Ozone–Induced Bronchial Hyperreactivity in Guinea Pigs", Pulmonary Pharm. 1992, 5, 39.

Yoneda et al., "The Antiproliferate Effects of Tyrosine Kinase Inhibitors Tyrphostins on a Human Squamous Cell Carcinoma in Vitro and in Nude Mice" Cancer Research 51: 4430–4435 (1991).

Miyaura, N. et al., "The Palladium–Catalyzed Cross–Coupling Reaction of Phenylboronic Acid with Ahloarenes in the Prescence of Bases", *Synthetic Communications* 1981, 11(7), 513–519.

Sakakibara, K. et al., "Preparation of N–pyridyl–4–(benzyloxy)Benzamides as Cardiotonics", *Chem. Abstr.* 1988, 108, No. 131583p.

Tsutsumi, K. et al., "Preparation of (Dialkoxyphosphinoylmethyl)benzamides as Antihyperlipidemics", *Chem. Abstr.* 1990, 113, No. 6599a.

TRI-SUBSTITUTED PHENYL DERIVATIVES AND PROCESSES FOR THEIR PREPARATION

This invention relates to a novel series of tri-substituted phenyl derivatives, to processes for their preparation, to pharmaceutical compositions containing them, and to their use in medicine.

Many hormones and neurotransmitters modulate tissue function by elevating intra-cellular levels of adenosine 3', 5'-cyclic monophosphate (cAMP). The cellular levels of cAMP are regulated by mechanisms which control synthesis and breakdown. The synthesis of cAMP is controlled by adenyl cyclase which may be directly activated by agents such as forskolin or indirectly activated by the binding of specific agonists to cell surface receptors which are coupled to adenyl cyclase. The breakdown of cAMP is controlled by a family of phosphodiesterase (PDE) isoenzymes, which also control the breakdown of guanosine 3', 5'-cyclic monophosphate (cGMP). To date, seven members of the family have been described (PDE I–VII) the distribution of which varies from tissue to tissue. This suggests that specific inhibitors of PDE isoenzymes could achieve differential elevation of cAMP in different tissues, [for reviews of PDE distribution, structure, function and regulation, see Beavo & Reifsnyder (1990) TIPS, 11: 150–155 and Nicholson et al (1991) TIPS, 12: 19–27].

There is clear evidence that elevation of cAMP in inflammatory leukocytes leads to inhibition of their activation. Furthermore, elevation of cAMP in airway smooth muscle has a spasmolytic effect. In these tissues, PDE IV plays a major role in the hydrolysis of cAMP. It can be expected, therefore, that selective inhibitors of PDE IV would have therapeutic effects in inflammatory diseases such as asthma, by achieving both anti-inflammatory and bronchodilator effects.

The design of PDE IV inhibitors has met with limited success to date, in that many of the potential PDE IV inhibitors which have been synthesised have lacked potency and/or have been capable of inhibiting more than one type of PDE isoenzyme in a non-selective manner. Lack of a selective action has been a particular problem given the widespread role of cAMP in vivo and what is needed are potent selective PDE IV inhibitors with an inhibitory action against PDE IV and little or no action against other PDE isoenzymes.

We have now found a novel series of tri-substituted phenyl derivatives, members of which are potent inhibitors of PDE IV at concentrations at which they have little or no inhibitory action on other PDE isoenzymes. These compounds inhibit the human recombinant PDE IV enzyme and also elevate cAMP in isolated leukocytes. The compounds of the invention are therefore of use in medicine, especially in the prophylaxis and treatment of asthma.

Thus according to one aspect of the invention, we provide a compound of formula (1)

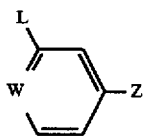

(1)

wherein

=W— is (1) =C(Y)— where Y is a halogen atom, or an alkyl or —$XR^a$ group where X is —O—, —$S(O)_m$— [where m is zero or an integer of value 1 or 2], or —$N(R^b)$— [where $R^b$ is a hydrogen atom or an optionally substituted alkyl group] and $R^a$ is a hydrogen atom or an optionally substituted alkyl group or, (2) =N—;

L is a —XR, [where R is an optionally substituted alkyl, alkenyl, cycloalkyl or cyloalkenyl group], —$C(R^{11})$=$C(R^1)(R^2)$ or [—$CH(R^1)]_n CH(R^1)(R^2)$ group where $R^{11}$ is a hydrogen or a fluorine atom or a methyl group, and $R^1$ and $R^2$, which may be the same or different, is each a hydrogen or fluorine atom or an optionally substituted alkyl, alkenyl, alkynyl, alkoxy, alkylthio, —$CO_2R^8$, [where $R^8$ is a hydrogen atom or an optionally substituted alkyl, aralkyl, or aryl group], —$CONR^9R^{10}$ [where $R^9$ and $R^{10}$, which may be the same or different are as defined for $R^8$], —$CSNR^9R^{10}$, —CN or —$NO_2$ group, or $R^1$ and $R^2$ together with the C atom to which they are attached are linked to form an optionally substituted cycloalkyl or cycloalkenyl group and n is zero or the integer 1;

Z is a group (A), or (B):

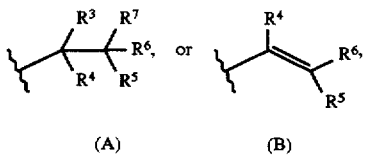

(A)            (B)

wherein $R^3$ is a hydrogen or a fluorine atom, an optionally substituted straight or branched alkyl group, or a hydroxyl group;

$R^4$ is a hydrogen atom or group —$(CH_2)_t Ar$ [where t is zero or an integer 1, 2 or 3 and Ar is a monocyclic or bicyclic aryl group, optionally containing one or more heteroatoms selected from oxygen, sulphur or nitrogen atoms] or a group —$(CH_2)_t$—Ar—$(L^1)_n$—Ar' [where $L^1$ is a divalent linking group and Ar' is Ar, —COAr, —$SO_2Ar$, —$SO_2NHAr$, —$SO_2N(Alk^1)Ar$ [where $Alk^1$ is a straight or branched $C_{1-6}$ alkylene, $C_{2-6}$ alkenylene or $C_{2-6}$ alkynylene chain optionally interrupted by one, two or three —O— or —S— atoms or —$S(O)p$— (where p is an integer 1 or 2) or —$N(R_p)$— groups], —$SO_2N[Ar]_2$, —CONHAr, —$CON(Alk^1)Ar$, —CON $[Ar]_2$, —$NAlk^1 SO_2Ar$, —$NHSO_2Ar$, —$N[SO_2Ar]_2$, —$NHSO_2NHAr$, —$NAlk^1SO_2NHAr$, —$NHSO_2N(Alk^1)Ar$, —$NAlk^1 SO_2NAlk^1 Ar$, —$NHSO_2N[Ar]_2$, —$NAlk^1 SO_2N[Ar]_2$, —NHC(O)Ar, —$NAlk^1C(O)Ar$, —$N[C(O)Ar]_2$, —NHC(O)NHAr, —$NAlk^1C(O)$ NHAr, —$NHC(O)N(Alk^1)Ar$, —$NAlk^1C(O)N(Alk^1)$ Ar, —NHC(O)OAr, —$NAlk^1 C(O)OAr$, —C(S)NHAr, —$C(S)NAlk^1Ar$, —$C(S)NAlk^1Ar$, —$C(S)N[Ar]_2$, —NHC(S)Ar, —$NAlk^1C(S)Ar$, —$N[C(S)Ar]_2$, —NHC(S)NHAr, —$NAlk^1C(S)NHAr$, —NHC(S) $NAlk^1Ar$, —$NAlk^1C(S)Nalk^1Ar$, —$SO_2NHet$ [where —NHet is an optionally substituted $C_{5-7}$ heterocyclic amino group optionally containing one or more other —O— or —S— atoms or —$N(R^b)$—, —C(O)— or —C(S)— groups], —CONHet, —CSNHet, —$NHSO_2NHet$, —NHC(O)NHet, —NHC(S)NHet, —$SO_2NH(Het')$ [where Het' is an optionally substituted $C_{5-7}$monocyclic carbocyclic group optionally containing one or more —O— or —S— atoms or —$N(R^b)$— groups], —CONH(Het'), —CSNH(Het'), —$NHSO_2NH(Het')$, —NHC(O)NHHet' or —NHC(S) NHHet'];

$R^5$ is a —$(CH_2)_r Ar$ or —$(CH_2)_r$—Ar—$(L^1)_n$—Ar' group, provided that when $R^5$ is a —$(CH_2)_r Ar$ group, =W— is =C(Y)— and L is —XR, then $R^4$ is a group —(CH$_2$)$_r$—Ar—(L$^1$)$_n$Ar';

$R^6$ is a hydrogen or a fluorine atom, or an optionally substituted alkyl group;

$R^7$ is a hydrogen or a fluorine atom, an optionally substituted straight or branched alkyl group or an $OR^c$ group where $R^c$ is a hydrogen atom or an optionally substituted alkyl or alkenyl group, or an alkoxyalkyl, alkanoyl, formyl, carboxamido or thiocarboxamido group; and the salts, solvates, hydrates, prodrugs and N-oxides thereof.

It will be appreciated that certain compounds of formula (1) may have one or more chiral centres, depending on the nature of the groups L, $R^1$, $R^2$, $R^3$, $R^4$, $R^5$, $R^6$ and $R^7$. Where one or more chiral centres is present, enantiomers or diastereomers may exist, and the invention is to be understood to extend to all such enantiomers, diastereomers and mixtures thereof, including racemates.

Compounds of formula (1) wherein L is a —C($R^{11}$)=C($R^1$)($R^2$) group and/or Z is the group (B), may exist as geometric isomers depending on the nature of the groups $R^1$, $R^2$, $R^4$, $R^5$, $R^6$ and $R^{11}$ and the invention is to be understood to extend to all such isomers and mixtures thereof.

In the compounds of formula (1), when =W— is =C(Y)— and Y is a halogen atom Y may be for example a fluorine, chlorine, bromine or iodine atom.

When W in the compounds of formula (1) is a group =C(Y)— and Y is —XR$^a$, $R^a$ may be, for example, a hydrogen atom or an optionally substituted straight or branched alkyl group, for example, an optionally substituted $C_{1-6}$alkyl group, such as a methyl, ethyl, n-propyl or i-propyl group. Optional substituents which may be present on $R^a$ groups include one or more halogen atoms, e.g. fluorine, or chlorine atoms. Particular $R^a$ groups include for example —CH$_2$F, —CH$_2$Cl, —CHF$_2$, —CHCl$_2$, —CF$_3$ or —CCl$_3$ groups.

When =W— in the compounds of formula (1) is a group =C (Y)— where —Y is —N($R^b$), =W— may be a =C(NH$_2$)—, =C(NHCH$_3$)— or =C(NHC$_2$H$_5$)— group.

In compounds of formula (1), X may be an oxygen or a sulphur atom, or a group —S(O)—, —S(O)$_2$—, —NH— or $C_{1-6}$ alkylamino, for example a $C^{1-3}$ alkylamino, e.g. methylamino [—N(CH$_3$)—] or ethylamino [—N(C$_2$H$_5$)—] group.

Alkyl groups represented by Y, R, $R^1$, $R^2$, or $R^b$ in the compounds of formula (1) include optionally substituted straight or branched $C^{1-6}$ alkyl groups optionally interrupted by one or more X atoms or groups. Particular examples include $C^{1-3}$ alkyl groups such as methyl or ethyl groups. Optional substituents on these groups include one, two or three substituents selected from halogen atoms, e.g. fluorine, chlorine, bromine or iodine atoms, or hydroxyl or $C^{1-6}$ alkoxy e.g. $C^{1-3}$ alkoxy such as methoxy or ethoxy or —CO$_2$R$^8$, —CONR$^9$R$^{10}$, —CSNR$^9$R$^{10}$ or —ON groups.

Alkenyl groups represented by $R^1$ or $R^2$ in the compounds of formula (1) include optionally substituted straight or branched $C_{2-6}$alkenyl groups optionally interrupted by one or more X atoms or groups. Particular examples include ethenyl, propen-1-yl and 2-methylpropen-1-yl groups. Optional substituents include those described above in relation to alkyl groups represented by the groups $R^1$ or $R^2$.

Alkynyl groups represented by $R^1$ or $R^2$ in compounds of formula (1) include optionally substituted straight or branched $C^{2-6}$alkynyl groups optionally interrupted by one or more X atoms or groups. Particular examples include ethynyl and propyn-1-yl groups. Optional substituents include those described above in relation to alkyl groups represented by the groups $R^1$ or $R^2$.

When $R^1$ or $R^2$ in compounds of formula (1) is an alkoxy or alkylthio group it may be for example an optionally substituted straight or branched $C^{1-6}$ alkoxy or $C^{1-6}$alkylthio group optionally interrupted by one or more X atoms or groups. Particular examples include $C_{1-3}$alkoxy, e.g. methoxy or ethoxy, or $C_{1-3}$alkylthio e.g. methylthio or ethylthio groups. Optional substituents include those described above in relation to alkyl groups represented by the groups $R^1$ or $R^2$.

When $R^1$ and $R^2$ together with the carbon atom to which they are attached in the compounds of formula (1) are linked to form a cycloalkyl or cycloalkenyl group, the group may be for example a $C_{3-8}$cycloalkyl group such as a cyclobutyl, cyclopentyl or cyclohexyl group or a $C_{3-8}$ cycloalkenyl group containing for example one or two double bonds such as a 2-cyclo-buten-1-yl, 2-cyclopenten-1-yl, 3-cyclopenten-1-yl, 2,4-cyclopentadien-1-yl, 2-cyclohexen-1-yl, 3-cyclohexen-1-yl, 2,4-cyclohexadien-1-yl or 3,5-cyclohexadien-1-yl group, each cycloalkyl or cycloalkenyl group being optionally substituted by one, two or three substituents selected from halogen atoms, e.g. fluorine, chlorine, bromine or iodine atoms, straight or branched $C_{1-6}$alkyl e.g. $C_{1-3}$alkyl such as methyl or ethyl, hydroxyl or $C_{1-6}$alkoxy e.g. $C_{1-3}$alkoxy such as methoxy or ethoxy groups.

When R in the compounds of formula (1) is an optionally substituted cycloalkyl or cycloalkenyl group it may be for example a $C_{3-8}$cycloalkyl group such as a cyclobutyl, cyclopentyl or cyclohexyl group or a $C_{3-8}$cycloalkenyl group containing for example one or two double bonds such as a 2-cyclobuten-1-yl, 2-cyclopenten-1-yl, 3-cyclopenten-1-yl, 2,4-cyclopentadien-1-yl, 2-cyclohexen-1-yl, 3-cyclohexen-1-yl, 2,4-cyclohexadien-1-yl or 3,5-cyclohexadien-1-yl group, each cycloalkyl or cycloalkenyl group being optionally substituted by one, two or three substituents selected from halogen atoms, e.g. fluorine, chlorine, bromine or iodine atoms, straight or branched $C_{1-6}$alkyl e.g. $C_{1-3}$alkyl such as methyl or ethyl, hydroxyl or $C_{1-6}$alkoxy e.g. $C^{1-3}$alkoxy such as methoxy or ethoxy groups.

When the group $R^7$ in compounds of formula (1) is an $OR^c$ group it may be for example a hydroxyl group; or a group —OR$^c$ where $R^c$ is an optionally substituted straight or branched $C_{1-6}$alkyl group, e.g. a $C_{1-3}$alkyl group such as a methyl or ethyl group, a $C_{2-6}$alkenyl group such as an ethenyl or 2-propen-1-yl group, a $C_{1-3}$alkoxy $C_{1-3}$alkyl group such as a methoxymethyl, ethoxymethyl or ethoxyethyl group, a $C_{1-6}$alkanoyl, e.g. $C_{1-3}$alkanoyl group such as an acetyl group, or a formyl [HC(O)—], carboxamido (CONR$^{12}$R$^{12a}$) or thiocarboxamido (CSNR$^{12}$R$^{12a}$) group, where $R^{12}$ and $R^{12a}$ in each instance may be the same or different and is each a hydrogen atom or an optionally substituted straight or branched $C_{1-6}$alkyl, e.g. $C_{1-3}$alkyl group such as methyl or ethyl group. Optional substituents which may be present on such $R^c$, $R^{12}$ or $R^{12a}$ groups include those described below in relation to the alkyl groups $R^6$ or $R^7$.

Alkyl groups represented by $R^3$, $R^6$ or $R^7$ in compounds of formula (1) include optionally substituted straight or branched $C_{1-6}$alkyl groups, e.g. $C_{1-3}$ alkyl groups such as methyl, ethyl, n-propyl or i-propyl groups. Optional substituents which may be present on these groups include one or more halogen atoms, e.g. fluorine, chlorine, bromine or iodine atoms, or hydroxyl or $C_{1-6}$alkoxy e.g. $C_{1-3}$alkoxy such as methoxy or ethoxy groups.

When the group $R^6$ in compounds of formula (1) is a halogen atom it may be for example a fluorine, chlorine, bromine or iodine atom.

When $R^1$ or $R^2$ is a —$CO_2R^8$, —$CONR^9R^{10}$ or $CSNR^9R^{10}$ group it may be for example a —$CO_2H$, —$CONH_2$ or —$CSNH_2$ group or a group —$CO_2R^8$, —$CONR^9R^{10}$, —$CSNR^9R^{10}$, —$CONHR^{10}$, or —$CSNHR^{10}$ where $R^8$, $R^9$ and $R^{10}$ where present is a $C_{1-3}$alkyl group such as methyl or ethyl group, a $C_{6-12}$aryl group, for example an optionally substituted phenyl, or a 1- or 2-naphthyl group, or a $C_{6-12}$aryl $C_{1-3}$alkyl group such as an optionally substituted benzyl or phenethyl group. Optional substituents which may be present on these aryl groups include $R^{13}$ substituents discussed below in relation to the group Ar.

In the compounds of formula (1), the groups —$(CH_2)_rAr$ and —$(CH_2)_rAr(L^1)_nAr'$ when present may be —Ar, —$CH_2Ar$, —$(CH_2)_2Ar$, —$(CH_2)_3Ar$—, —Ar—Ar', —Ar—$L^1$—Ar', —$CH_2ArAr'$, —$CH_2ArL^1Ar'$, —$(CH_2)_2ArAr'$, —$(CH_2)_2ArL^1Ar'$, —$(CH_2)_3ArAr'$ or —$(CH_2)_3ArL^1Ar'$ groups.

Monocyclic or bicyclic aryl groups represented by the group Ar or Ar' in compounds of formula (1) include for example $C_{6-12}$ optionally substituted aryl groups, for example optionally substituted phenyl, 1-or 2-naphthyl, indenyl or isoindenyl groups.

When the monocyclic or bicyclic aryl group Ar or Ar' contains one or more heteroatoms, Ar or Ar' may be for example a $C_{1-9}$ optionally substituted heteroaryl group containing for example one, two, three or four heteroatoms selected from oxygen, sulphur or nitrogen atoms. In general, Ar or Ar' heteroaryl groups may be for example monocyclic or bicyclic heteroaryl groups. Monocyclic heteroaryl groups include for example five- or six-membered heteroaryl groups containing one, two, three or four heteroatoms selected from oxygen, sulphur or nitrogen atoms. Bicyclic heteroaryl groups include for example nine- or ten-membered heteroaryl groups containing one, two or more heteroatoms selected from oxygen, sulphur or nitrogen atoms.

Examples of heteroaryl groups represented by Ar or Ar' include pyrrolyl, furyl, thienyl, imidazoly, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, isobenzothienyl, indolyl, isoindolyl, benzimidazolyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl and 5,6,7,8-tetrahydroisoquinolinyl. Example of bicyclic heteroaryl groups include quinolinyl or isoquinolinyl groups.

The heteroaryl group represented by Ar or Ar' may be attached to the remainder of the molecule of formula (1) through any ring carbon or heteroatom as appropriate. Thus, for example, when the group Ar or Ar' is a pyridyl group it may be a 2-pyridyl, 3-pyridyl or 4-pyridyl group. When it is a thienyl group it may be a 2-thienyl or 3-thienyl group, and, similarly, when it is a furyl group it may be a 2-furyl or 3-furyl group. In another example, when the group Ar or Ar' is a quinolinyl group it may be a 2-, 3-, 4-, 5-, 6-, 7- or 8-quinolinyl and when it is an isoquinolinyl, it may be a 1-, 3-, 4-, 5-, 6-, 7- or 8-isoquinolinyl group.

When in compounds of formula (1) the Ar or Ar' group is a nitrogen-containing heterocycle it may be possible to form quaternary salts, for example N-alkyl quaternary salts and the invention is to be understood to extend to such salts.

Thus for example when the group Ar or Ar' is a pyridyl group, pyridinium salts may be formed, for example N-alkylpyridinium salts such as N-methylpyridinium.

The aryl or heteroaryl groups represented by Ar or Ar' in compounds of formula (1) may each optionally be substituted by one, two, three or more substituents [$R^{13}$]. The substituent $R^{13}$ may be selected from an atom or group $R^{14}$ or —$Alk^2(R^{14})m$ wherein $R^{14}$ is a halogen atom, or an amino (—$NH_2$), substituted amino, nitro, cyano, hydroxyl (—OH), substituted hydroxyl, cycloalkoxy, formyl [HC(O)—], carboxyl (—$CO_2H$), esterified carboxyl, thiol (—SH), substituted thiol, —C(O)$Alk^2$, —$SO_3H$, —$SO_2Alk^2$, —$SO_2NH_2$, —$SO_2NHAlk^2$, —$SO_2N[Alk^2]_2$, —$CONH_2$, —$CONHAlk^2$, $CON[Alk^2]_2$—$NHSO_2H$, —$NAlk^2SO_2H$, —$NHSO_2Alk^2$, —$NAlk^2SO_2Alk^2$, —$N[SO_2Alk^2]_2$— $NHSO_2NH_2$, —$NAlk^2SO_2NH_2$, —$NHSO_2NHAlk^2$, —$NAlk^2SO_2NHAlk^2$, —$NHSO_2N[Alk^2]_2$, —$NAlk^2SO_2N$ $[Alk^2]_2$, —NHC(O)H, —NHC(O)$Alk^2$, —$NAlk^2C(O)H$, —$NAlk^2C(O)Alk^2$, —$N[C(O)Alk^2]_2$, —NHC(O)OH, —$NHC(O)OAlk^2$, —$NAlk^2C(O)OH$, —$NAlk^2C(O)OAlk^2$, —$NHCONH_2$, —$NHCONHAlk^2$, —$NHCON[Alk^2]_2$, —$NAlk^2CON[Alk^2]_2$, —$NAlk^2CONH[Alk^2]$, —$NAlk^2CONH_2$, —C(S)H, —C(S)$Alk^2$, —$CSNH_2$, —$CSNHAlk^2$, —$CSN[Alk^2]_2$, —NHC(S)H, —$NHCSAlk^2$, —$NAlk^2C(S)H$, —$NAlk^2C(S)Alk^2$, —$N[C(S)Alk^2]_2$, —$N[C(O)Alk^2]SO_2H$, —$NHCSNH_2$, —$NHCSNHAlk^2$, —$NHCSN[Alk^2]_2$, —$NAlk^2CSN[Alk^2]_2$, —$NAlk^2CSNHAlk^2$, —$NAlk^2CSNH_2$, or —$N[C(O)Alk^2]SO_2Alk^2$ group, $Alk^2$ is a straight or branched $C_{1-6}$ alkylene, $C_{2-6}$alkenylene, or $C_{2-6}$alkynylene chain optionally interrupted by one, two, or three —O—, or —S— atoms or —S(O)p—, [where p is an integer 1 or 2] or —$N(R^8)$— groups; and m is zero or an integer 1,2 or 3.

When in the group —$Alk^2(R^{14})_m$ m is an integer 1, 2 or 3, it is to be understood that the substituent or substituents $R^{14}$ may be present on any suitable carbon atom in —$Alk^2$. Where more than one $R^{14}$ substituent is present these may be the same or different and may be present on the same or different carbon atom in $Alk^2$. Clearly, when m is zero and no substituent $R^{14}$ is present or when $Alk^2$ forms part of a group such as —$SO_2Alk^2$ the alkylene, alkenylene or alkynylene chain represented by $Alk^2$ becomes an alkyl, alkenyl or alkynyl group.

When $R^{14}$ is a substituted amino group it may be a group —$NH[Alk^2(R^{14a})_m]$ [where $Alk^2$ and m are as defined above and $R^{14a}$ is as defined above for $R^{14}$ but is not a substituted amino, a substituted hydroxyl or a substituted thiol group] or a group —$N[Alk^2(R^{14a})_m]_2$ wherein each —$Alk^2(R^{14a})_m$ group is the same or different.

When $R^{14}$ is a halogen atom it may be for example a fluorine, chlorine, bromine, or iodine atom.

When $R^{14}$ is a cycloalkoxy group it may be for example a $C_{5-7}$cycloalkoxy group such as a cyclopentyloxy or cyclohexyloxy group.

When $R^{14}$ is a substituted hydroxyl or substituted thiol group it may be a group —$OAlk^2(R^{14a})_m$ or —$SAlk^2(R^{14a})_m$ respectively, where $Alk^2$, $R^{14a}$ and m are as just defined.

Esterified carboxyl groups represented by the group $R^{14}$ include groups of formula —$CO_2Alk^3$ wherein $Alk^3$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{18}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy $C_{1-8}$alkyl group such as an optionally substituted phenyloxymethyl, phenyloxyethyl, 1-naphthyloxymethyl, or 2-naphthyloxymethyl group; an optionally substituted $C_{1-8}$alkanoyloxy $C_{1-8}$alkyl group, such as a pivaloyloxymethyl, propionyloxyethyl or propionyloxypropyl group; or a $C_{6-12}$aroyloxy $C_{1-8}$alkyl group such as an optionally substituted benzoyloxyethyl or benzoyloxy-propyl group. Optional substituents present on the Alk$^3$ group include $R^{13}$ substituents described above.

It will be appreciated that the group Ar or Ar' may be attached to the remainder of the molecule of formula (1) through either a ring carbon atom or heteroatom.

Particular examples of the chain Alk$^2$ when present include methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N(R$^b$)— groups.

Particularly useful atoms or groups represented by $R^{13}$ include fluorine, chlorine, bromine or iodine atoms, or $C_{1-6}$alkyl, e.g. methyl or ethyl, $C_{1-6}$alkylamino, e.g. methylamino or ethylamino, $C_{1-6}$hydroxyalkyl, e.g. hydroxymethyl or hydroxyethyl, $C_{1-6}$alkylthiol e.g. methylthiol or ethylthiol, $C_{1-6}$alkoxy, e.g. methoxy or ethoxy, $C_{5-7}$cycloalkoxy, e.g. cyclopentyloxy, halo $C_{1-6}$alkyl, e.g. trifluoromethyl, $C_{1-6}$alkylamino, e.g. methylamino or ethylamino, amino (—NH$_2$), amino $C_{1-6}$alkyl, e.g. aminomethyl or aminoethyl, $C_{1-6}$dialkylamino, e.g. dimethylamino or diethylamino, nitro, cyano, hydroxyl (—OH), formyl [HC(O)—], carboxyl (—CO$_2$H), —CO$_2$Alk$^3$ [where Alk$^3$ is as defined above], $C_{1-6}$alkanoyl e.g. acetyl, thiol (—SH), thio $C_{1-6}$alkyl, e.g. thiomethyl or thioethyl, sulphonyl (—SO$_3$H), $C_{1-6}$alkylsulphonyl, e.g. methylsulphonyl, aminosulphonyl (—SO$_2$NH$_2$), $C_{1-6}$alkylaminosulphonyl, e.g. methylaminosulphonyl or ethylaminosulphonyl, $C_{1-6}$dialkylamino-sulphonyl, e.g. dimethylaminosulphonyl or diethylaminosulphonyl, carboxamido (—CONH$_2$), $C_{1-6}$alkylaminocarbonyl, e.g. methylamino-carbonyl or ethylaminocarbonyl, $C_{1-6}$dialkylaminocarbonyl, e.g. dimethyl-aminocarbonyl or diethylaminocarbonyl, sulphonylamino (—NHSO$_2$H), $C_{1-6}$alkylsulphonylamino, e.g. methylsulphonylamino or ethylsulphonyl-amino, $C_{1-6}$dialkylsulphonylamino, e.g. dimethylsulphonylamino or diethyl-sulphonylamino, aminosulphonylamino (—NHSO$_2$NH$_2$), $C_{1-6}$alkylamino-sulphonylamino, e.g. methylaminosulphonylamino or ethylamino-sulphonylamino, $C_{1-6}$dialkylaminosulphonylamino, e.g. dimethylamino-sulphonylamino or diethylaminosulphonylamino, $C_{1-6}$alkanoylamino, e.g. acetylamino, $C_{1-6}$alkanoylamino $C_{1-6}$alkyl, e.g. acetylaminomethyl or $C_{1-6}$ alkoxycarbonylamino, e.g. methoxycarbonylamino, ethoxycarbonylamino or t-butoxycarbonylamino thiocarboxamido (—CSNH$_2$), $C_{1-6}$ alkylamino-thiocarbonyl, e.g. methylaminothiocarbonyl or ethylaminothiocarbonyl, $C_{1-6}$dialkylaminothiocarbonyl, e.g. dimethylaminothiocarbonyl or diethyl-aminothiocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylamino-carbonylamino, aminothiocarbonylamino, $C_{1-6}$alkylaminothiocarbonyl-amino, e.g. methylaminothiocarbonylamino or ethylaminothiocarbonyl-amino, $C_{1-6}$ dialkylaminothiocarbonylamino, e.g. dimethylaminothiocarbonylamino, or diethylaminothiocarbonylamino, aminocarbonyl/$C_{1-6}$alkyl amino, e.g. aminocarbonylmethylamino or aminocarbonylethylamino, aminothiocarbonyl $C_{1-6}$alkylamino e.g. aminothiocarbonylmethylamino or aminothiocarbonylethylamino, formylamino $C_{1-6}$alkylsulphonylamino, e.g. formylaminomethylsulphonylamino or formyl-aminoethylsulphonylamino, thioformylamino $C_{1-6}$alkylsulphonylamino, e.g. thioformylaminomethyl-sulphonylamino or thioformylethylsulphonylamino, $C_{1-6}$acylaminosulphonylamino, e.g. acetylaminosulphonylamino, $C_{1-6}$thioacylaminosulphonyl-amino, e.g. thioacetylaminosulphonylamino groups.

Where desired, two $R^{13}$ substituents may be linked together to form a cyclic group such as a cyclic ether, e.g. a $C_{2-6}$alkylenedioxy group such as ethylenedioxy.

It will be appreciated that where two or more $R^{13}$ substituents are present, these need not necessarily be the same atoms and/or groups. The $R^{13}$ substituents may be present at any ring carbon atom away from that attached to the rest of the molecule of formula (1). Thus, for example, in phenyl groups represented by Ar or Ar' any substituent may be present at the 2-, 3-, 4-, 5- or 6-positions relative to the ring carbon atom attached to the remainder of the molecule.

In the compounds of formula (1), when the group —(CH$_2$)$_r$Ar(L$^1$)$_n$Ar' is present in R$^4$ and/or R$^5$, the linker group L$^1$ may be any divalent linking group. Particular examples of L$^1$ groups which may be present in compounds of the invention include groups of formula —(Alk$^4$)$_r$(X$^a$)$_s$ (Alk$^5$)$_t$—where Alk$^4$ and Alk$^5$ is each an optionally substituted straight or branched $C_{1-6}$alkylene, $C^{2-6}$alkenylene or $C_{2-6}$alkynylene chain optionally interrupted by one or more, e.g. one, two or three heteroatoms or carbocyclic or heteroatom-containing groups, X$^a$ is an —O— or —S— atom or a —S(O)—, —S(O)$_2$— or —N(R$^b$)— group, r is zero or the integer 1,t is zero or the integer 1 and s is zero or the integer 1, provided that when one of r, s, or t is zero at least one of the remainder is the integer 1.

The heteroatoms which may interrupt the Alk$^4$ or Alk$^5$ chains include for example —O— or —S— atoms. Carbocyclic groups include for example cycloalkyl, e.g. cyclopentyl or cyclohexyl, or cycloalkenyl e.g. cyclopentenyl or cyclohexenyl, groups. Particular heteroatom-containing groups which may interrupt Alk$^4$ or Alk$^5$ include oxygen-, sulphur- or nitrogen-containing groups such as —S(O)—, —S(O)$_2$—, —N(R$^b$)—, —C(O)—, —C(S)—, —C(NR$^b$)—, —CON(R$^b$)—, —CSN(R$^b$)—, —N(R$^b$)CO—, —N(R$^b$)CS—, —SON(R$^b$), —SO$_2$N(R$^b$)—, —N(R$^b$)SO—, —N(R$^b$)SO$_2$—, —N(R$^b$)SO$_2$N(R$^b$)—, —N(R$^b$)SON(R$^b$)—, or —N(R$^b$)CON(R$^b$)— groups. It will be appreciated that when the chains Alk$^4$ or Alk$^5$ are interrupted by two or more heteroatoms, carbocyclic or heteroatom-containing groups, such atoms or groups may be adjacent to one another, for example to form a group —N(R$^b$)—C(NR$^b$)—N(R$^b$)— or —O— CONH—.

Optional substituents which may be present on Alk$^4$ or Alk$^5$ chains include those described above in relation to the group R$^1$ when it is an alkyl group.

The group —(L$^1$)$_n$Ar' may be attached to the group Ar through any available carbon or heteroatoms present in the two groups. Thus, for example, when Ar is a phenyl group, —(L$^1$)$_n$Ar' may be attached through a carbon or heteroatom in —(L$^1$)$_n$Ar' to a carbon atom in Ar at the 2-, 3-, 4-, 5-, or 6-position relative to the Ar carbon atom attached to the remainder of the molecule.

In the group (L$^1$)$_n$Ar' particular examples of Alk$^4$ or Alk$^5$ include optionally substituted methylene, ethylene, propylene, butylene, ethenylene, 2-propenylene, 2-butenylene, 3-butenylene, ethenylene, 2-propynylene, 2-butynylene or 3-butynylene chains, optionally interrupted by one, two or three heteroatoms, carbocyclic or heteroatom-containing groups as described above.

Particular examples of the group —(L$^1$)$_n$Ar' include the groups —Alk$^4$Ar', —XAr', —Alk$^4$XAr' and —XAlk$^5$Ar', especially for example —CH$_2$Ar', —(CH$_2$)$_2$Ar', —(CH$_2$)$_3$Ar', —CH$_2$OCH$_2$Ar', —CH$_2$SCH$_2$Ar', —CH$_2$N(R$^b$)CH$_2$Ar', —CH=CHAr', —CH$_2$CH=CHAr', —OAr', —SAr', —N(R$^b$)Ar', —CH$_2$OAr', —CH$_2$SAr', —CH$_2$N(R$^b$)Ar', —CH$_2$CH$_2$OAr', —OCH$_2$Ar', —O(CH$_2$)$_2$Ar', —SCH$_2$Ar', —S(CH$_2$)$_2$Ar', —N(R$^b$)CH$_2$Ar' and —N(R$^b$)(CH$_2$)$_2$Ar'.

In these particular groups, Ar' may be as described herein, and may be especially an optionally substituted C$_{6-12}$aryl or C$_{1-9}$heteroaryl group, in particular an optionally substituted phenyl or pyridyl group or a —COPh (where Ph is an optionally substituted phenyl group), —SO$_2$Ph, —SONHPh, —SO$_2$N(Alk$^1$)Ph, —SO$_2$N[Ph]$_2$, —CONHPh, —CON(Alk$^1$)Ph, —CON[Ph]$_2$, —NAlk$^1$SO$_2$Ph, —NHSO$_2$N(Alk$^1$)Ph, —NAlk$^1$SO$_2$Alk$^1$ Ph, —NHSO$_2$N[Ph]$_2$, —NAlk$^1$SO$_2$N[Ph]$_2$, —NHC(O)Ph, —NAlk$^1$COPh, —NC(O)N[Ph]$_2$, —NHC(O)NHPh, —NAlk$^1$C(O)NHPh, —NHC(O)N(Alk$^1$)Ph, —NAlk$^1$C(O)N(Alk$^1$)Ph, —NHC(O)OPh, —NAlk$^1$C(O)OPh, —C(S)NHPh, —C(S)NAlk$^1$Ph, —N(S)N[Ph]$_2$, —NHC(S)Ph, —NAlk$^1$C(S)Ph, —N[C(S)Ph]$_2$, —NHC(S)NHPh, —NAlk$^1$C(S)NHPh, —NHC(S)NAlk$^1$Ph, or —NAlk$^1$C(S)NAlk$^1$Ph group. In these groups, the group Alk$^1$ may in particular be a methyl or ethyl group.

When in R$^4$ and/or R$^5$ a -NHet group is present this may be for example a pyrrolidinyl, pyrazolidinyl, piperidinyl, morpholinyl, piperazinyl or thiomorpholinyl group. Optional substituents that may be present in such groups include R$^{13}$ substituents described above in relation to Ar or Ar' groups.

When in R$^4$ and/or R$^5$ a Het' group is present this may be for example a pyrrolidinyl, pyrazolidinyl, piperidinyl, morpholinyl, piperazinyl, thiomorpholinyl, cyclopentyl, or cyclohexyl group. Optional substituents that may be present on such groups include R$^{13}$ substituents described above.

In the compounds of formula (1), when an ester group is present, for example a group CO$_2$R$^8$ or —CO$_2$Alk$^3$ this may advantageously be a metabolically labile ester.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Prodrugs of compounds of formula (1) include those compounds, for example esters, alcohols or aminos, which are convertible in vivo by metabolic means, e.g. by hydrolysis, reduction, oxidation or trans-esterification, to compounds of formula (1).

Particularly useful salts of compounds according to the invention include pharmaceutically acceptable salts, especially acid addition pharmaceutically acceptable salts.

In the compounds of formula (1) the group =W— is preferably a =C(Y)— group. In compounds of this type Y is preferably a —XR$^a$ group where X is —O— and R$^a$ is an optionally substituted ethyl group or, especially, an optionally substituted methyl group. Especially useful substituents which may be present on R$^a$ groups include one, two or three fluorine or chlorine atoms.

One particularly useful group of compounds of the invention has the formula (1) where L is a group —XR. In compounds of this type X is preferably —O—. The group R in these compounds is preferably an optionally substituted cycloalkyl group, particularly an optionally substituted cyclopentyl group, and is, especially a cyclopentyl group.

In another group of compounds of formula (1) L is preferably a —CH=C(R$^1$)(R$^2$) group. In compounds of this type R$^1$ and R$^2$ are preferably linked together with the C atom to which they are attached to form an optionally substituted cycloalkyl or cycloalkenyl group, especially a substituted cyclopentyl or cyclohexyl or, especially, a cyclopentyl or cyclohexyl group.

The groups R$^4$ and R$^5$ in compounds of formula (1) is each, independently, preferably a —(CH$_2$)$_r$Ar or —(CH$_2$)$_r$Ar—(L$^1$)$_n$—Ar' group, particularly a CH$_2$Ar or —CH$_2$Ar(L$^1$)$_n$Ar' group or especially an —Ar, Ar—Ar' or ArL$^1$Ar' group. Particularly useful R$^4$ or R$^5$ groups of this type include those groups in which Ar or Ar' is a monocyclic aryl group optionally containing one or more heteroatoms selected from oxygen, sulphur, or, in particular, nitrogen atoms, and optionally substituted by one, two, three or more R$^{13}$ substituents. In these compounds, when the group represented by Ar or Ar' is a heteroaryl group it is preferably a nitrogen-containing monocyclic heteroaryl group, especially a six-membered nitrogen-containing heteroaryl group. Thus, in one preferred example, the groups R$^4$ and R$^5$ may each contain a six-membered nitrogen-containing heteroaryl Ar or Ar' group. In another preferred example R$^4$ may contain a monocyclic aryl group or a monocyclic or bicyclic heteroaryl group Ar or Ar' containing one or more oxygen, sulphur or nitrogen atoms and R$^5$ may contain a sixmembered nitrogen-containing heteroaryl group Ar or Ar'. In these examples, the six-membered nitrogen-containing heteroaryl group may be an optionally substituted pyridyl, pyridazinyl, pyrimidinyl, pyrazinyl or imidazolyl group. Particular examples include optionally substituted 2-pyridyl, 3-pyridyl, 5-imidazolyl, or, especially, 4-pyridyl, 3-pyridazinyl, 4-pyridazinyl, 5-pyridazinyl, 2-pyrimidinyl, 4-pyrimidinyl, 5-pyrimidinyl, 2-pyrazinyl or 3-pyrazinyl. The monocyclic aryl group may be a phenyl group or a substituted phenyl group, and the monocyclic or bicyclic heteroaryl group containing one or more oxygen, sulphur or nitrogen atom may be an optionally substituted 2-furyl, 3-furyl, 2-thienyl, 3-thienyl, 2-thiazolyl, 2-benzo(b)thiophenyl, 2-benzo(b)furyl or 4-isoquinolinyl group.

In another preference relating to R$^4$ groups of the just mentioned particular types, Ar' is a —NHC(O)NHPh (where Ph is as just described, —NHCH$_3$C(O)NHPh, —NHC(O)NCH$_3$Ph, —NCH$_3$C(O)NCH$_3$Ph, —COPh, —NHSO$_2$NHPh, —NCH$_3$SO$_2$NHPh, —NCH$_3$SO$_2$NCH$_3$Ph, —NHCOPh, —NCH$_3$COPh or —NHSO$_2$Ph group, particularly in those instances where L$_1$ is a —CH$_2$— group.

In general in compounds of formula (1) when R$^4$ and/or R$^5$ contains a substituted phenyl group it may be for example a mono-, di- or trisubstituted phenyl group in which the substituent is an atom or group R$^{13}$ as defined above. When the R$^4$ and/or R$^5$ group contains a monosubstituted phenyl group the substituent may be in the 2-, or preferably 3-, or especially 4-position relative to the ring carbon atom attached to the remainder of the molecule. When the $R^4$ and/or $R^5$ group contains a disubstituted phenyl group, the substituents may be in the 2,6 position relative to the ring carbon atom attached to the remainder of the molecule.

Particularly useful substituents $R^{13}$ which may be present on Ar groups in $R^4$ and $R^5$, especially on phenyl groups, include halogen atoms or alkyl, haloalkyl, amino, substituted amino, nitro, —NHSO$_2$NH$_2$, —NHSO$_2$NHCH$_3$, —NHSO$_2$N(CH$_3$)$_2$, —NHCOCH$_3$, —NHC(O)NH$_2$, —NCH$_3$C(O)NH$_2$, —NHC(O)NHCH$_3$, —NHC(O)NHCH$_2$CH$_3$, or —NHC(O)N(CH$_3$)$_2$ groups, each of said atoms or groups being optinally separated from the remainder of the Ar group by a group Alk$^2$ as defined above.

When in compounds of formula (1) $R^4$ and/or $R^5$ contains a substituted pyridyl group it may be for example a mono-or disubstituted pyridyl group, such as a mono- or disubstituted 2-pyridyl, 3-pyridyl or especially 4-pyridyl group substituted by one or two atoms or groups $R^{13}$ as defined above, in particular one or two halogen atoms such as fluorine or chlorine atoms, or methyl, methoxy, hydroxyl or nitro groups. Particularly useful pyridyl groups of these types are 3-monosubstituted-4-pyridyl or 3,5-disubstituted-4-pyridyl, or 2- or 4-monosubstituted-3-pyridyl or 2,4-disubstituted-3-pyridyl groups.

A particularly useful group of compounds of formula (1) has the formula (2):

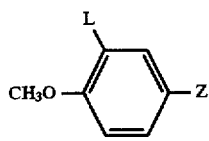

(2)

where —L is a OR, where R is an optionally substituted cycloalkyl group, —CH=C(R$^1$)(R$^2$) or —CH$_2$CH(R$^1$)(R$^2$) group where R$^1$ and R$^2$ are linked together with the carbon atom to which they are attached to form a cycloalkyl group; Z is as defined for formula (1); and the salts, solvates, hydrates, prodrugs and N-oxides thereof.

In the compounds of formulae (1) or (2) where Z is the group (A), one preferred group of compounds are those where the group $R^3$ is a hydrogen atom; the group $R^6$ is a methyl group, or especially a hydrogen atom; the group $R^7$ is a methyl group, or especially a hydrogen atom; and $R^4$ and $R^5$ are as defined for formula (1). In compounds of this type $R^6$ and $R^7$ is each especially a hydrogen atom.

In general in compounds of formulae (1) or (2) the group Z is preferably a group of type (A). In compounds of this type $R^3$, $R^6$ and $R^7$ is each especially a hydrogen atom, $R^5$ is in particular an optionally substituted pyridyl group, especially a 4-pyridyl group and $R^4$ is in particular a —(CH$_2$)$_r$—Ar—(L$^1$)$_n$—Ar' group, especially a —Ar—(L$^1$)$_n$—Ar' group. Particular examples of —Ar—(L$^1$)$_n$—Ar' groups include —Ar—Ar, —Ar—O—Ar, —Ar—CH$_2$—Ar, —Ar—(CH$_2$)$_2$Ar, —Ar—NHC(O)NHAr, —Ar—CH$_2$NHC(O)NHAr, —Ar—COAr, —Ar—CH$_2$COAr, —Ar—NHSO$_2$NHAr, —Ar—CH$_2$NHSO$_2$NHAr, —Ar—NHSO$_2$Ar, —Ar—CH$_2$NHSO$_2$Ar, —Ar—NCH$_3$C(O)NHAr, —Ar—CH$_2$NCH$_3$C(O)NHAr, —Ar—NCH$_3$SO$_2$NHAr or —Ar—CH$_2$NCH$_3$SO$_2$NHAr groups. In these groups Ar may in particular be an optionally substituted phenyl group. Optional substituents include for example, halogen atoms, e.g. chlorine or fluorine atoms, alkyl, e.g. methyl, haloalkyl, e.g. trifluoromethnyl, amino, substituted amino, e.g. methylamino, ethylamino, dimethylamino, nitro, —NHSO$_2$NH$_2$, —NHSO$_2$NHCH$_3$, —NHSO$_2$ N(CH$_3$)$_2$, —NHCOCH$_3$, —NHC(O)NH$_2$, —NCH$_3$C(O)NH$_2$, —NHC(O)NHCH$_3$, —NHC(O) NHCH$_2$CH$_3$, or —NHC(O)N(CH$_3$)$_2$ groups, each of said atoms or groups being optionally separated from the remainder of the phenyl group by a —CH$_2$— group.

In the above examples, when Ar is a phenyl group, the —(L$^1$)$_n$Ar group or any other optional substituent may be attached to any available ring carbon atom away from that attached to the remainder of the compound of formula (1).

Particularly useful compounds according to the invention are:

(±)-4-{2-(3-Cyclopentyloxy-4-methoxyphenyl)-2-[4-(4-trifluoromethylphenyl) phenylethyl]}pyridine;

(±)-4-[2-(4-Benzyloxyphenyl)-2-(3-cyclopentyloxy-4-methoxyphenyl)ethyl]pyridine;

(±)-4-{2-(3-Cyclopentyloxy-4-methoxyphenyl)-2-[4-(4-nitrophenyloxy)-phenyl]ethyl}pyridine; (E) and (Z) isomers of 4-[2-(3-Cyclopentyloxy-4-methoxyphenyl) ethenyl]-3-(phenylethyl)pyridine);

(±)-4-[2-(3-Cyclopentyloxy-4-methoxyphenyl)ethyl]-3-(phenylethyl)pyridine;

(±)-4-{2-[4-(4-Aminophenyloxy)phenyl]-2-(3-cyclopentyloxy-4-methoxy-phenyl)ethyl}pyridine;

(±)-4-{2-[4-(4-Acetamidophenyloxy)phenyl]-2-(3-cyclopentyloxy-4-methoxyphenyl)ethyl]pyridine;

(±)-4-{2-(3-Cyclopentyloxy-4-methoxyphenyl)-2-[4-(4—N', N'-dimethylamino-sulphonylaminophenyl) phenyloxy]ethyl}pyridine;

(±)-4-{2-(3-Cyclopentyloxy-4-methoxyphenyl)-2-[4-(4-methylsulphonyl-aminophenyl)phenyloxy]ethyl}pyridine;

(±)-4-[2-(3-Cyclopentyloxy-4-methoxyphenyl)-2-(4'-methyl-4-biphenyl)-ethyl]pyridine;

(±)-N-{3-[1-(3-Cyclopentyloxy-4-methoxyphenyl)-2-(4-pyridyl)ethyl]phenyl-methyl}-N'phenylurea; or each isomer of the resolved enantioners, and the salts, solvates, hydrates, prodrugs and 11-oxides thereof.

Compounds according to the invention are selective and potent inhibitors of PDE IV. The ability of the compounds to act in this way may be simply determined by the tests described in the Examples hereinafter.

Particular uses to which the compounds of the invention may be put include the prophylaxis and treatment of asthma, especially inflamed lung associated with asthma, cystic fibrosis, or in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restenosis and artherosclerosis.

Compounds of the invention may also suppress neurogenic inflammation through elevation of cAMP in sensory neurones. They are, therefore, analgesic, anti-tussive and anti-hyperalgesic in inflammatory diseases associated with irritation and pain.

Compounds according to the invention may also elevate cAMP in lymphocytes and thereby suppress unwanted lymphocyte activation in immune-based diseases such as rheumatoid arthritis, ankylosing spondylitis, transplant rejection and graft versus host disease.

Compounds according to the invention may also reduce gastric acid secretion and therefore can be used to treat conditions associated with hypersecretion.

Compounds of the invention may suppress cytokine synthesis by inflammatory cells in response to immune or infectious stimulation. They are, therefore, useful in the treatment of bacterial, fungal or viral induced sepsis and septic shock in which cytokines such as tumour necrosis factor (TNF) are key mediators. Also compounds of the invention may suppress inflammation and pyrexia due to cytokines and are, therefore, useful in the treatment of inflammation and cytokine-mediated chronic tissue degeneration which occurs in diseases such as rheumatoid or osteoarthritis.

Over-production of cytokines such as TNF in bacterial, fungal or viral infections or in diseases such as cancer, leads to cachexia and muscle wasting. Compounds of the invention may ameliorate these symptoms with a consequent enhancement of quality of life.

Compounds of the invention may also elevate cAMP in certain areas of the brain and thereby counteract depression and memory impairment.

Compounds of the invention may suppress cell proliferation in certain tumour cells and can be used, therefore, to prevent tumour growth and invasion of normal tissues.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, nonaqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formulae (1) and (2) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formulae (1) and (2) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular inflammatory condition will vary depending on the compound chosen, and the condition of the patient to be treated. In general, however, daily dosages may range from around 100 ng/kg to 100 mg/kg. e.g. around 0.01 mg/kg to 40 mg/kg body weight for oral or buccal administration, from around long/kg to 50 mg/kg body weight for parenteral administration and around 0.05 mg to around 1000 mg e.g. around 0.5 mg to around 1000 mg for nasal administration or administration by inhalation or insufflation.

The compounds according to the invention may be prepared by the following processes. The symbols W, L, Z, X, $R^1$, $R^2$, $R^3$, $R^4$, $R^5$, $R^6$, $R^7$ and $R^{11}$ when used in the formulae below are to be understood to represent those groups described above in relation to formula (1) unless otherwise indicated. In the reactions described below it may be necessary to protect reactive functional groups, for example hydroxy, amino, thio, or carboxy groups, where these are desired in the final product, to avoid their unwanted participation in the reactions. Conventional protecting groups may be used in accordance with standard practice [see, for example, Green, T. W. in "Protective Groups in Organic Synthesis" John Wiley and Sons, 1981].

Thus, according to a further aspect of the invention, compounds of general formula (1) where L is a —$C(R^{11})$=$C(R^1)(R^2)$ group, $R^{11}$ is a hydrogen atom or a methyl group and $R^3$ when present is a hydrogen atom, may be prepared by coupling a compound of formula (3)

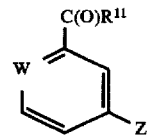

(3)

where $p^{11}$ is as described above with an olefination agent.

Particular examples of olefination agents include phosphonium salts such as compounds $(R^1)(R^2)CHP(D)_3Hal$ where Hal is a halogen atom, such as a bromine atom, and D is an optionally substituted alkyl, e.g. methyl, or aryl, especially phenyl, group; phosphoranes $(R^1)(R^2)C$=$P(D)_3$; phosphonates $(DO)_2P(O)CH(R^1)(R^2)$; or silane derivatives, for example compounds of formula $(D)_3SiC(R^1)(R^2)$, e.g. trialkylsilanes such as $(CH_3)_3SiC(R^1)(R^2)$.

Bases for use in the above reaction include organometallic bases, for example, an organolithium compound such as an alkyllithium e.g. n-butyllithium, a hydride, such as sodium or potassium hydride or an alkoxide, such as a sodium alkoxide, e.g. sodium methoxide.

The reaction may be performed in a suitable solvent, for example a polar aprotic solvent, such as an alkyl sulphoxide, e.g. methyl sulphoxide, an amide such as N,N- dimethylformamide or hexamethylphosphorous triamide; a non-polar solvent, such as an ether, e.g. tetrahydrofuran or diethyl ether or an aromatic solvent such as benzene, toluene or xylene; or a polar protic solvent, such as an alcohol, for example ethanol. Preferably the reaction is carried out at a low temperature, for example from around −78° C. to around room temperature.

The olefination agents used in this reaction are either known compounds or may be prepared from known starting materials using reagents and conditions similar to those used to prepare the known compounds. For example, a phosphorane may be prepared in situ by reaction of a phosphonium salt with a base of the type described above. In another example, a phosphonate may be prepared by reacting a halide $(R^1)(R^2)$CHHal with a phosphite $(DO)_3P$, as described in the Arbuzov reaction. Silane derivatives may be prepared by reaction of a halosilane $(D)_3$SiHal with a base, such as lithium diisopropylamide, in a solvent, such as an ether, for example a cyclic ether, e.g. tetrahydrofuran, at low temperature, e.g. around −10° C.

According to a further aspect of the invention compounds of formula (1) where L is a group —$C(R^{11})$=$CH(R^1)$ and $R^1$ is an optionally substituted alkyl, alkenyl or alkynyl group may also be prepared by reaction of an intermediate of formula (3) with an organometallic reagent, followed by dehydration of the corresponding alcohol.

Examples of organometallic reagents include organolithium $R^1Li$ or organomagnesium $R^1MgHal$ reagents. The reaction with the organometallic reagent may be performed in a solvent such as an ether, such as diethyl ether or for example a cyclic ether such as tetrahydrofuran, at a low temperature for example −10° C. to room temperature. The dehydration may be performed using an acid, for example an organic acid such as p-toluene sulphonic acid or trifluoroacetic acid, in the presence of a base, such as an amine, e.g. triethylamine.

Intermediates of formula (3) where $R^{11}$ is a methyl group, may be prepared by reacting an intermediate of formula (3) where $R^{11}$ is a hydrogen atom with an organometallic reagent, such as methyllithium or $CH_3MgHal$, using the conditions just described followed by oxidation of the resulting alcohol, using an oxidising agent, e.g. manganese dioxide.

Intermediates of formula (3) where $R^{11}$ is a hydrogen atom may be prepared by deprotecting a protected aldehyde of formula (4)

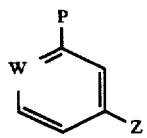

(4)

where P is a protected aldehyde group, e.g. a dioxanyl group, using acid hydrolysis e.g. by reaction with trifluoroacetic acid or p-toluene sulphonic acid, in the presence of a solvent, e.g. acetone, or a mixture of solvents, e.g. chloroform and water.

Intermediates of formula (4) where Z is a group (A) in which $R^3$ is a hydroxyl group may be prepared by reacting a ketone of formula (5)

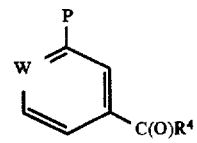

(5)

with a reagent $R^5CHR^6R^7$ using a base, such as an organometallic base, for example an organolithium reagent e.g. n-butyllithium, in a solvent, such as an ether, e.g. tetrahydrofuran, at around −70° C. to room temperature.

Intermediates of formula (5) may be prepared by oxidation of an alcohol of formula (6)

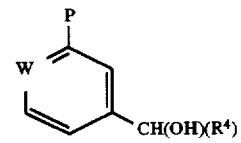

(6)

using an oxidising agent, such as manganese (IV) oxide, in a solvent, such as dichloromethane, at room temperature.

Intermediates of formula (6) may be prepared by reacting a halide of formula (8) described below with an aldehyde $R^4CHO$, in the presence of a base, such as n-butyllithium, in a solvent, e.g. tetrahydrofuran, at a temperature from around −70° C. to room temperature.

Intermediates of formula (4) where Z is a group (A) in which $R^3$ is a hydrogen atom may be prepared by hydrogenation of an intermediate of formula (4) where Z is a group (B) using the reagents and conditions described hereinafter for the hydrogenation of a compound of formula (1) where L is a —$C(R^{11})$=$C(R^1)(R^2)$ group to give a compound of formula (1) where L is a —$CH(R^{11})$—$CH(R^1)(R^2)$ group.

Intermediates of formula (4) where Z is the group (B) may be prepared by dehydrating an intermediate of formula (4) where Z is the group (A) and $R^3$ is a hydroxyl group, by using an acid, e.g. trifluoroacetic acid, in the presence of a base, such as an amine, e.g. triethylamine, in a solvent, such as dichloromethane, at a low temperature, e.g. around −10° C.

Intermediates of formula (4) where Z is a group (B) may be prepared by condensing an intermediate of formula (7)

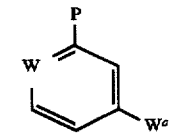

(7)

where (a) Wa is a —$C(O)R^4$ group, with a compound $R^5CH_2R^6$; or where (b) Wa is a —$CH_2R^4$ group with an aldehyde or ketone $R^5COR^6$; or where (c) Wa is a —$C(O)R^4$ group with a silane derivative $(Alk^a)_3SiCH(R^5)(R^6)$, where $Alk^a$ is an alkyl group; in each instance in the presence of a base or an acid in a suitable solvent.

Bases for use in these reactions include inorganic bases, for example alkali and alkaline earth metal bases, e.g. hydroxides, such as sodium or potassium hydroxide; alkoxides, for example sodium ethoxide; organic bases, for example amines such as piperidine; and organolithium bases, such as alkyllithium, e.g. n-butyllithium bases. Suitable solvents include alcohols such as ethanol, or ethers such as tetrahydrofuran. Acids for use in the reactions include organic acids, e.g. carboxylic acids such as acetic acid.

The reactions may be performed at any suitable temperature, for example from around −78° C. to ambient temperature or to the reflux temperature depending on the nature of the starting materials.

In general, the base, acid, solvent and reaction conditions may be selected depending on the nature of the starting materials, from a range of known alternatives for reactions of this type.

In silane derivatives of formula $(Alk^a)_3SiCH(R^5)(R^6)$, $Alk^a$ may be for example a $C^{1-6}$alkyl group such as a methyl group. Derivatives of this type may be prepared for example by reacting a compound $R^5$—$CH_2$—$R^6$ with a silane derivative, such as a chlorotrialkylsilane, e.g. chlorotrimethyl-silane in the presence of a base, e.g. lithium diisopropylamide, in a solvent, e.g. tetrahydrofuran, at a low temperature, e.g. around −10° C.

The starting materials $R^5COR^6$ and $R^5CH_2R^6$ are either known compounds or may be prepared from known starting materials by methods analogous to those used for the preparation of the known compounds.

Intermediates of formula (7) where —$W^a$ is a —$C(O)R^4$ group may be prepared by reacting an aldehyde of formula (7) where —Wa is a —CHO group with an organometallic reagent in a solvent, e.g. tetrahydrofuran, at low temperature, e.g. around 10° C., followed by oxidation of the resulting alcohol with an oxidising agent, such as manganese dioxide, in a solvent, e.g. dichloromethane.

Intermediates of formula (7) where —Wa is —CHO may be prepared by reacting a compound of formula (8)

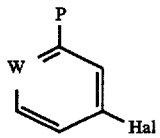

(8)

where Hal is a halogen atom, e.g. a bromine atom, with an organometallic reagent, such as n-butyllithium, in a solvent, such as an amide, e.g. dimethylformamide, at a low temperature, e.g. below −60° C.

Intermediates of formula (8) may be prepared by protecting an aldehyde or ketone of formula (9)

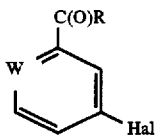

(9)

where Hal is a halogen atom, e.g. a bromine atom with an aldehyde or ketone protecting group, using for example a suitable diol, e.g. 1,3-propanediol, in the presence of an acid catalyst, e.g. 4-toluenesulphonic acid, in a solvent, such as an aromatic solvent, e.g. toluene, at an elevated temperature such as the reflux temperature.

In general, this reaction may be used when it is desired to protect an aldehyde in any intermediate described herein.

Intermediates of formula (9) are either known compounds or may be prepared in a similar manner to the known compounds.

In another process according to the invention, compounds of formula (1) where Z is a group (B) may be prepared by reacting a compound of formula (10)

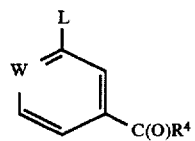

(10)

with a phosphonate ester $(R'O)(OR'')P(O)CH(R^5)(R^6)$ [where R' and R", which may be the same or different is an alkyl, or aralkyl group] in the presence of a base in a suitable solvent.

Suitable bases include organometallic bases such as organolithium, e.g. n-butyllithium, alkoxides, for example alkali metal alkoxides such as sodium ethoxide or sodium methoxide and a hydride such as potassium hydride or sodium hydride. Solvents include ethers, e.g. diethylether or cyclic ethers such as tetrahydrofuran and alcohol, e.g. methanol or ethanol.

The phosphonate derivatives used in this reaction are either known compounds or may be prepared by reacting a phosphite $P(OR')_2(OR'')$ with a compound $R^5CHR^6Hal$ [where Hal is a halogen atom, for example a bromine atom] using conventional methods.

Intermediates of formula (10) where $R^4$ is as described for compounds of formula (1) but is not a hydrogen atom may be prepared by reaction of the corresponding compound where $R^4$ is a hydrogen atom with an organometallic reagent, followed by oxidation, as described previously for the preparation of intermediates of formula (7) where $W^a$ is a —$C(O)R^4$ group.

Intermediates of formula (10) where $R^4$ is a hydrogen atom may be prepared by reacting a halide of formula (11)

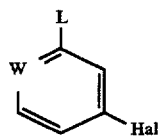

(11)

where Hal is a halogen atom, e.g. a bromine or chlorine atom with an organometallic reagent using the same reagents and conditions described above for the preparation of intermediates of formula (7) where Wa is —CHO from intermediates of formula (8).

Intermediates of formula (11) where L is a —$C(R^{11})$=$C(R^1)(R^2)$ group may be prepared by coupling a compound of formula (9) with a phosphonium salt $(R^1)(R^2)CHP(D)_3Hal$ as described above for the preparation of compounds of formula (1) from intermediate of formula (3).

Intermediates of formula (11) where L is an —XR group may be prepared by alkylation of a corresponding compound where L is —XH using a compound RHal (where Hal is a halogen atom) in the presence of a base in a solvent such as dimethylformamide at ambient temperature or above, e.g. around 40° C. to 50° C. Intermediates of formula (11) where L is —XH are either known compounds or may be prepared from known starting materials using conventional procedures, for example when X is —O—from the corresponding aldehyde by oxidation.

In yet another process according to the invention, a compound of formula (1) where one or both of $R^4$ and $R^5$ is a —$(CH_2)_rAr(L^1)_nAr'$ group may be prepared by coupling a compound of formula (12).

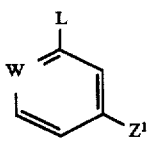

(12)

[where Z' is as defined for Z in formula (1) except that one or both of $R^4$ and $R^5$ is a group —(CH$_2$)$_r$ArE where E is a boronic acid —B(OH)$_2$ or a tin reagent Sn(R$^{15}$)$_3$, where $R^{15}$ is an alkyl group, for example a methyl group], with a reagent Ar' (L$^1$)$_n$L$^2$ where L$^2$ is a leaving group, in the presence of a complex metal catalyst.

Particular leaving groups L$^2$ include for example halogen atoms, e.g. bromine, iodine or chlorine atoms and an alkyl sulphonate, such as trifluoromethanesulphonate. Particular tin reagents include those compounds for example where $R^{15}$ in the formula Sn(R$^{15}$)$_3$ is a methyl group.

Suitable catalysts include heavy metal catalysts, for example palladium catalysts, such as tetrakis (triphenylphosphine)palladium. The reaction may be performed in an inert solvent, for example an aromatic hydrocarbon such as toluene or benzene, or an ether, such as dimethoxyethane or dioxane, if necessary in the presence of a base, e.g. an alkali carbonate such as sodium carbonate, at an elevated temperature, e.g. the reflux temperature. In general, the metal catalyst and reaction conditions may be selected, depending on the nature of the compound of formula (12) and/or the compound of Ar'(L$^1$)$_n$L$^2$ from a range of known alternatives for reactions of this type [see for example Miyaura, N et al, Synth. Comm. (1981), 11, 513; Thompson, W. J. and Gaudino, J., J. Org. Chem. (1984), 49, 5237 and Sharp, M. J. et al, Tetrahedron Lett. (1987), 28, 5093].

Intermediates Ar'(L$^1$)$_n$L$^2$ are either known compounds or may be prepared from known starting materials by methods analogous to those used for the preparation of the known compounds. Thus, for example, where it is desired to obtain a compound Ar'(L$^1$)$_n$L$^2$ where L$^2$ is a halogen atom such as bromine or chlorine atom and this compound is not readily available, such a compound may be prepared by diazotisation of the corresponding amine using for example a nitrite such as sodium nitrite in an aqueous acid at a low temperature followed by reaction with an appropriate copper (I) halide in an aqueous acid.

Intermediates of formula (12) may be prepared by halogen-metal exchange with a base such as n-butyl or t-butyllithium followed by reaction with a borate such as triisopropylborate or a tin reagent (R$^{15}$)$_3$SnHal, where R is as described above and Hal is a halogen atom, such as chlorine atom, optionally at a low temperature e.g. around $-70°$ C., in a solvent such as tetrahydrofuran.

In another example of a process according to the invention, a compound of formula (1) where one or both of $R^4$ and $R^5$ is a group —(CH$_2$)$_r$ArL$^1$Ar' where L$^1$ is —X$^a$(Alk$^5$)$_t$— may be prepared by reacting a compound of formula (12) where Z' is as defined for Z in formula (1), except that one or both of $R^4$ and $R^5$ is a group —(CH$_2$)$_r$ArX$^a$H with a reagent Ar' (Alk$^5$)$_t$L$^2$, where L$^2$ is a leaving group, as described above.

The reaction may be performed in the presence of a base, for example triethylamine or potassium tert-butoxide, in a solvent such as dichloromethane or tetrahydrofuran, at a suitable temperature, e.g. room temperature.

According to a further aspect of the invention, compounds of formula (1) where L is a group —CH(R$^1$)(R$^2$) where R$^2$ is a —CO$_2$R$^8$ or —CONR$^9$R$^{10}$ group may be prepared by reacting a compound of formula (13)

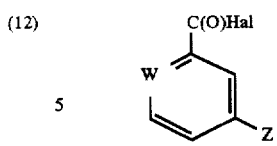

(13)

where Hal is a halogen atom, such as a chlorine or a bromine atom, with a diazoalkane CH(R$^1$)N$_2$ followed by reaction with R$^8$OH or R$^9$R$^{10}$NH in the presence of silver oxide or a silver salt optionally in the presence of a base.

Intermediates of formula (13) may be prepared by oxidation of an intermediate of formula (3) where $R^{11}$ is a hydrogen atom, using an oxidising agent, such as permanganate or chromic acid, to give the corresponding carboxylic acid which is then reacted with a halide reagent, such as thionylchloride, phosphorous pentachloride or phosphorous pentabromide.

According to another aspect of the invention, a compound of formula (1) where L is a group —XR, $R^3$ is a hydroxyl group and $R^7$ is a hydrogen atom may be prepared by reaction of an intermediate of formula (10) with an organometallic reagent R$^5$R$^6$CHM, where M is a metal atom.

Metal atoms represented by M include, for example, a lithium atom.

The reaction may be performed in a solvent such as an ether, e.g. a cyclic ether such as tetrahydrofuran, at a low temperature, e.g. around $-70°$ C. to ambient temperature. This reaction is particularly suitable for the preparation of compounds of formula (1) wherein $R^5$ is an electron deficient group such as a 2- or 4-pyridyl group.

In another process according to the invention compounds of formula (1) wherein W is =N— and $R^7$ is a hydroxyl group may be prepared by reacting a compound of formula (14)

(14)

or its N-oxide
with a reagent R$^5$C(O)R$^6$ using the conditions described herein for the preparation of a compound of formula (1) from an intermediate of formula (10).

N-oxides of compounds of formula (14) may be prepared by reacting a compound of formula (14) with a hydrogen peroxide or a peroxyacid, e.g. peracetic acid, peroxymonophthalic acid, trifluoroacetic acid or metachloroperbenzoic acid in carboxylic acid solution, e.g. acetic acid, a halogenated solvent, e.g. dichloromethane or an ether such as tetrahydrofuran. It is to be understood that in this case the compound of formula (1) would be obtained as its N-oxide.

Reagents R$^5$C(O)R$^6$ are known compounds or may be prepared in a manner similar to the preparation of the known compounds.

Intermediates of formula (14) may be prepared by reacting a halide of formula (15)

(15)

where Hal is a halogen atom, e.g. a bromine, chlorine or iodine atom with a compound RXH, where X is —O—, —S— or —NH— in the presence of a base.

Bases used in this reaction include hydrides, such as sodium hydride, or an organometallic base, such as butyllithium in a solvent, such as an amide, for example dimethylformamide at a temperature from room temperature to above, e.g. 80° C.

Intermediates of formula (15) may be prepared by reacting the commercially available amine of formula (16)

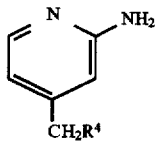 (16)

with nitrous acid (made in situ by reacting sodium nitrite with an acid, for example sulphuric acid or hydrobromic acid) to produce the diazonium salt. This in turn may be reacted with a haloacid, e.g. hydrobromic, hydrochloride or hydriodic acid if necessary in the presence of the corresponding copper (I) halide (CuBr or Cu I) or halogen e.g. $Br_2$, $Cl_2$ or $I_2$.

Compounds of formula (1) may be prepared by interconversion of another compound of formula (1). For example, a compound of formula (1) where L is a —$CH_2$—CH($R^1$)($R^2$) group may be prepared by hydrogenation of a compound of formula (1) where L is a —CH=C($R^1$)($R^2$) group. The hydrogenation may be performed using for example hydrogen in the presence of a cataylst. Suitable catalysts include metals such as platinum or palladium optionally supported on an inert carrier such as carbon or calcium carbonate; nickel, e.g. Raney nickel, or rhodium. The reaction may be performed in a suitable solvent, for example an alcohol such as methanol or ethanol, an ether such as tetrahydrofuran or dioxane, or an ester such as ethyl acetate, optionally in the presence of a base, for example a tertiary organic base such as triethylamine, at for example ambient temperature.

Alternatively, the reaction may be accomplished by transfer hydrogenation using an organic hydrogen donor and a transfer agent. Suitable hydrogen donors include for example acids, such as formic acid, formates, e.g. ammonium formate, alcohols, such as benzyl alcohol or ethylene glycol, hydrazine, and cycloalkenes such as cyclohexene or cyclohexadiene. The transfer agent may be for example a transition metal, for example palladium or platinum, optionally supported on an inert carrier as discussed above, nickel, e.g. Raney nickel, ruthenium, e.g. tris (triphenylphosphine) ruthenium chloride or copper. The reaction may generally be performed at an ambient or elevated temperature, optionally in the presence of a solvent, for example an alcohol such as ethanol or an acid such as acetic acid.

The same hydrogenation or transfer hydrogenation reagents and conditions may be used to also interconvert (a) compounds of formula (1) where L is a —XR group and Z is a group (B) to compounds of formula (1) where L is a —XR group and Z is a group (A) where $R^3$ and $R^7$ is each a hydrogen atom; and (b) compounds of formula (1) where a $NO_2$ group is present as a substituent on an Ar or Ar' group to compounds of formula (1) where a $NH_2$ group is present as a substituent on an Ar or Ar' group.

In another example of an interconversion process, compounds of formula (1) where Z is a group (A) in which $R^7$ is an $OR^c$ group where $R^c$ is an alkyl or alkenyl group, may be prepared by reacting a compound of formula (1) where Z is a group (A) in which $R^7$ is a —OH group, with a reagent $R^c$—OH, in the presence of an acid, such as sulphuric acid.

In yet another example of an interconversion process, compounds of formula (1) where Z is a group (A) in which $R^7$ is an $OR^c$ group where $R_c$ is a carboxamido or thiocarboxamido group may be prepared by reaction of a compound of formula (1) where Z is a group (A) in which $R^7$ is a —OH group, with an isocyanate $R^cN$=C=O or an isothiocyanate $R^cN$=C=S in the presence of a base, such as sodium hydride, in a solvent, such as tetrahydrofuran. Compounds $R^cN$=C=O and $R^cN$=C=S are known compounds or may be prepared using the reagents and conditions used for the preparation of the known compounds. When $R^cN$=C=S is not available, a compound of formula (1) where $R_c$ is a thiocarboxamido group may be prepared by interconverting a compound of formula (1) where $R_c$ is a carboxamido group using a thiation reagent, such as Lawesson's reagent [2,4-bis(4-methoxyphenyl)-1,3,2,4-dithiadiphosphetane-2,4-di-sulphide], in an aromatic solvent, such as xylene or toluene.

In a still further example of an interconversion process, a compound of formula (1) where Z is a group (A) in which $R^3$ is a fluorine atom may be prepared by reacting a compound of formula (1) where Z is a group (A) in which $R^3$ is a hydroxyl group, with a fluorinating reagent, such as diethylaminosulphur trifluoride (DAST), in a solvent, for example a chlorinated solvent, e.g. dichloromethane, at a low temperature, e.g. around 0° C.

In a still further example of an interconversion process, a compound of formula (1) where Z is a group (A) in which $R^3$ is an alkyl group, may be prepared by alkylation of a compound of formula (1) where Z is a group (A), and $R^3$ is a hydrogen atom, with a reagent $R^3L^1$ using a base, for example n-butyllithium or lithium diisopropylamide. In this process, $R^4$ in the starting material is preferably an electron withdrawing group.

A compound of formula (1) where L is a group —CH($R^1$)($R^2$) may also be prepared by interconversion of a compound of formula (1) where L is a —CH($R^1$)$CO_2H$ group. For example, a compound of formula (1) where L is a group —CH($R^1$)CONR$^9R^{10}$, may be prepared by reacting a compound of formula (1) where L is a group —CH($R^1$)$CO_2H$ (or an active derivative thereof, such as a —CH($R^1$)C(O)Hal group) with an amine $R^9R^{10}NH$ using standard conditions.

In another example of an interconversion process, a compound of formula (1) where L is a group —CH($R^1$)($R^2$) where $R^2$ is a nitrile group may be prepared (a) by dehydrogenating the corresponding compound of formula (1) where L is a group —CH($R^1$)$CH_2NH_2$ using for example nickel peroxide; or (b) by reacting the corresponding aldehyde [obtained by reduction of a compound of formula (1) where L is a group —CH($R^1$)$CO_2H$] using (i) Li in $MeNH_2$ or $NH_3$ followed by pyridinium chlorochromate; or (ii) borane-$Me_2S$ followed by pyridinium chlorochromate, with hydroxylamine hydrochloride, in a solvent, such as an amine, for example an aromatic amine, e.g. pyridine, followed by treatment with an acid, such as formic acid or hydrochloric acid.

According to a further interconversion process, a compound of formula (1) where Z is the group (B) may be prepared by dehydration of a corresponding compound of formula (1) where Z is a group (A) where $R^3$ or $R^7$ is a hydroxyl group using an acid- or base-catalysed elimination.

Suitable acids include for example phosphoric or sulphonic acids, e.g. 4-toluenesulphonic acid. The reaction may be performed in an inert organic solvent, for example a hydrocarbon such as toluene, at an elevated temperature, for example the reflux temperature. Base-catalysed elimination may be performed using for example trifluoroacetic anhydride in the presence of an organic base such as triethylamine at a low temperature, e.g. from around 0°C. to ambient temperature, in a solvent such as dichloromethane or tetrahydrofuran.

In yet another example of an interconversion process, a compound of formula (1) where Ar or Ar' is substituted by an amido, e.g. acetamido, or alkyl aminosulphonylamino e.g. dimethylaminosulphonylamino group may be prepared by reacting a compound of formula (1) wherein Ar or Ar' is substituted by an amino group using an anhydride, e.g. acetic anhydride, or a sulphamoyl halide, e.g. dimethylsulphamoyl chloride, in a solvent e.g. an amine such as pyridine, at room temperature.

In a still further example of an interconversion process, a compound of formula (1) where Ar or Ar' is substituted by an alkylsulphonylamino, e.g. methylsulphonylamino group, may be prepared by reacting a compound of formula (1) where Ar or Ar' is substituted by an amino group with an alkylsulphonylhalide, e.g. methanesulphonylchloride, in the presence of a base, e.g a tertiary amine such as triethylamine or N-methylmorpholine, in a solvent, e.g. a halogenated solvent such as dichloromethane.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate acid or base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral acid or base. Suitable chiral acids include, for example, tartaric acid and other tartrates such as dibenzoyl tartrates and ditoluoyl tartrates, sulphonates such as camphor sulphonates, mandelic acid and other mandelates and phosphates such as 1,1'-binaphthalene-2,2'-diyl hydrogen phosphate. The diastereomers may then be separated by any convenient means, for example by crystallisation and the desired enantiomer recovered, e.g. by treatment with an acid or base in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

The following Examples illustrate the invention. In the Examples, the following abbreviations are used: DME—ethylene glycol dimethyl ether; THF — tetrahydrofuran; $CH_2Cl_2$. dichloromethane; $Et_2O$ — diethyl ether; EtOH — ethanol; RT — room temperature; DMF — N, N-dimethylformamide; EtOAc — ethyl acetate; DMPU — 1,3-dimethyl-3,4,5,6-tetrahydro-2(1H)pyrimidinone; BuLi — butyllithium.

INTERMEDIATE 1
5-Bromo-2-methoxyphenol

The title compound was prepared as described in International Patent Specification No. WO 93/10118.

INTERMEDIATE 2
4-Bromo-2-cyclopentyloxyanisole

The title compound was prepared as described in International Patent Specification No. WO 94/10118.

INTERMEDIATE 3
(4-Bromophenyl)(3-cyclopentyloxy-4-methoxyphenyl)ketone

The title compound was prepared as described in International Patent Specification No. WO 94/14742.

INTERMEDIATE 4
4-[2-(4-Bromophenyl)-2-(3-cyclopentyloxy-4-methoxyphenyl)-2-hydroxyethyl]pyridine The title compound was prepared as described in International Patent Specification No. WO 94/14742.

INTERMEDIATE 5
(E) and (Z) isomers of 4-[2-(4-Bromophenyl)-2-(3-cyclopentyloxy-4-methoxyphenyl)ethenyl]pyridine The title compound was prepared as described in International Patent Specification No. WO 94/14742.

INTERMEDIATE 6
Acyl Sultam (1)

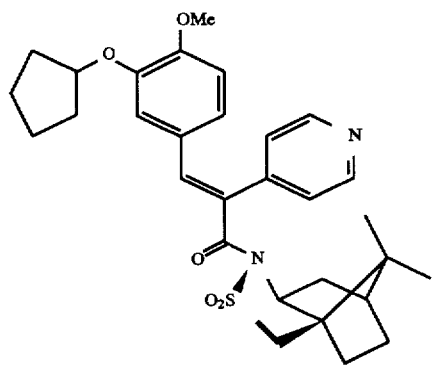

The sultam was synthesised as described in our International Patent Application No. PCT/GB 94/02799.

INTERMEDIATE 7
(1R,5S)-N-[(3R)-3-(4-Benzyloxyphenyl)-3-(3-cyclopentyloxy-4-methoxyphenyl)-2-(4-pyridyl)propanoyl]-10,10-dimethyl-3-thia-4-azatricylo[5.2.1.0$^{1,5}$]decane-3,3-dioxide

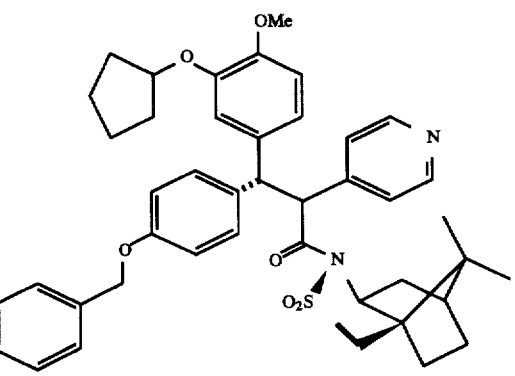

A solution of 4-bromobenzyloxybenzene (22.3 g, 84.9 mmol, 2.2 equiv) in THF (100 ml) was added to magnesium turnings (2.44 g, 101.9 mmol, 2.6 equiv) in THF (10 ml)

containing 1,2-dibromoethane (2 drops) and the mixture heated to reflux for 0.5 h. The cooled solution was added dropwise at −40° C. to a solution of Intermediate 6 (20.68 g, 38.6 mmol) in THF-Et$_2$O (1:5; 600 ml) and the mixture allowed to warm to −10° C. over 4 h. Ammonium chloride solution (10%; 150 ml) and EtOAc (300 ml) were added and the organic layer was separated and combined with further EtOAC portions (3×100 ml). The extract was dried (MgSO$_4$) and concentrated in vacuo and the yellow residue recrystallised from EtOH to afford the title compound (17.93 g) as a pale yellow solid. δH (CDCl$_3$) 0.69 (3H, s, MeCMe), 0.87 (3H, s, MeCMe), 1.15–1.35 (2H, br m), 1.4–1.5 (1H, br m), 1.5–2.0 (12H, br m), 3.31 (1H, d, J 13.8 Hz, CHSO$_2$), 3.44 (1H, d, J 13.8 Hz, CHSO$_2$), 3.65–3.75 (1H, m, NCH), 4.51 (1H, d, J 11.5HZ, CHCHO), 4.58 (1H, br m, OCH), 4.95–5.1 (3H, m, OCH$_2$ +CHCHO), 6.55–6.65 (3H, m, C$_6$H$_3$), 6.86 (2H, ca. d, J 8.7 Hz, 2×ArH ortho to benzyloxy), 7.25–7.45 (9H, m, C$_6$H$_5$+pyridine H$_3$, H$_5$ +2×ArH meta to benzyloxy), and 8.37 (2H, dd, J 4.5, 1.5 Hz, pyridine H$_2$, H$_6$).

INTERMEDIATE 8
(R)-4-[2-(3-Cyclopentyloxy-4-methoxyphenyl)-2-(4-hydroxyphenyl) ethyl]pyridine A mixture of the compound of Example 3 (9.35 g, 19.5 mmol), cyclohexadiene (25 ml, 195 mmol), and 10% Pd/C (1.0g) in EtOH (300ml) was heated to reflux for 2 h. The reaction mixture was filtered through Celite® and the filtrate and washings concentrated in vacuo to afford the title compound (7.6 g) as a white foam; δH (CDCl$_3$) 1.4–1.9 (1H, br m, (CH$_2$)$_4$), 3.2–3.35 (2H, m, CHCH$_2$), 3.79 (3H, s, OMe), 4.05 (1H, ca. t, J ca. 7.8 Hz CHCH$_2$), 4.65 (1H, br m, OCH), 6.6–6.8 (5H, m, C$_6$H$_3$+2×ArH ortho to OH), 6.9–7.0 (4H, m, pyridine H$_3$, H$_5$+2×ArH meta to OH) and 8.36 (2H, ca. d, J ca. 4.5 Hz pyridine H$_2$, H$_6$).

INTERMEDIATE 9
4-Methyl-3-pyridinecarboxaldehyde n-BuLi (1.6 M in hexanes) (2.2 mmol, 1.37 ml) was added dropwise to a stirred solution of N,N,N'-trimethylethylenediamine (2.4 mmol, 0.245 g) in THF at −78° C. A solution of 3-pyridinecarboxaldehyde (2 mmol, 0.214 g) in THF was added and the mixture stirred for 15 min before adding a further portion of n-BuLi (1.6M in hexanes) (4 mmol, 2.5 ml). After stirring for 2 h at −70° C., iodomethane was added, the mixture stirred at RT for 30 min, then poured into aqueous NaCl solution, extracted twice with Et$_2$O, dried (MgSO$_4$), filtered and concentrated in vacuo. The residue was subjected to chromatography (SiO$_2$; Et$_2$O) to afford the title compound as an oil.

INTERMEDIATE 10
(4-Methyl-3-phenylethenyl)pyridine

Benzyltriphenylphosphonium bromide (mixture with sodium amide) (99 mmol, 4.96 g) was dissolved in THF at RT and stirred for 30 min. A red solution was obtained. Intermediate 9 (8.3 mmol, 1g) in solution in THF was added, the reaction mixture stirred for 16 h then poured into aqueous NaHCO$_3$ solution, extracted twice with CH$_2$Cl$_2$, dried (MgSO$_4$), filtered and concentrated in vacua. The residue was subjected to chromatography (SiO$_2$;Et$_2$O) to afford the title compound (1.5 g) as an oily compound.

INTERMEDIATE 11
(4-Methyl-3-phenylethyl)pyridine

A stirred solution of Intermediate 10 (1.8 g) in EtOH was hydrogenated using H$_2$—Pd/C for 16 h. The title compound was obtained as an oil.

INTERMEDIATE 12
3-Cyclopentyloxy-4-methoxybenzaldehyde

The title compound was prepared as described in International Patent Specification No. WO 94/20455.

INTERMEDIATE 13
2-Bromo-4-methylpyridine

To an aqueous solution of 48% HBr (56.55 ml, 520.64 mmol) was slowly added 2-amino-4-methylpyridine (10 g, 92.47 mmol) at below −5° C. Bromine (14 ml, 274 mmol) was then added dropwise whilst maintaining the temperature below 0° C., followed by careful addition of a solution of sodium nitrite (17.5 g, 254 mmol) in water (20 ml) to keep the temperature below 5° C. After stirring for 1 hr, a solution of NaOH (37 g, 940 mmol) in H$_2$O (50 ml) was added at a temperature below 25° C. The reaction mixture was extracted with Et$_2$O (3×75 ml), the combined layer was washed (brine), dried (MgSO$_4$) then evaporated to dryness to give a crude oil. Flash chromatography (SiO$_2$;hexane/Et$_2$O, 50:50) afforded the title compound (10.2 g) as a yellow oil. δH (CDC$_3$) 2.45 (3H, s, ArCH$_3$), 7.00 (1H, d, pyridine H$_5$), 7.25 (1H, s, pyridine H$_3$), and 8.15 (1H, d, pyridine H$_6$). m/z 172 M+1), 174 (M+1).

INTERMEDIATE 14
2-Cyclopentyloxy-4-methylpyridine

To a cold (0° C.) suspension of sodium hydride (2 g, 50 mmol) in DMF (20 ml) was added dropwise cyclopentanol (4.99 ml, 55 mmol) and the solution allowed to warm to RT and stirred for 1 hr. Intermediate 13 (8.6 g, 49.67 mmol) was added dropwise and the reaction mixture heated at 80° C. for 2 hr. After cooling, H$_2$O (100 ml) was added, the mixture extracted into Et$_2$O (3×100 ml), washed (brine), dried (MgSO$_4$) then evaporated to dryness to give an orange oil. Chromatography (SiO$_2$; hexane/Et$_2$O, 50:50) afforded the title compound (7.5 g) as an orange oil. m/z 179 (M+1). δH (CDCl$_3$) 1.5–2.0 (8H, m, (CH$_2$)$_4$), 2.25 (3H, s, CH$_3$), 5.35 (1H, m, OCH), 6.45 (1H, s, pyridine H$_2$), 6.65 (1H, d, pyridineH$_5$), and 7.96 (1H, d, pyridine H6))

EXAMPLE 1 a) (E) and (Z)isomers of 4-{2-(3-Cyclopentyloxy-4-methoxy-phenyl)-2-[4-(trifluoromethylphenyl)phenyl]ethenyl}pyridine A mixture of Intermediate 5 (500 mg, 1.1 mmol) and tetrakis (triphenyl-phosphine) palladium in DME (20 ml) was allowed to stir at RT for 0.5 h. Sodium carbonate solution (2M; 1.5 ml, 3.0 mmol) and 4-trifluoromethylphenylboronic acid (190 mg, 1.0 mmol) was added and the reaction mixture heated to reflux for 18 h. The mixture was cooled, partitioned between water (10 ml) and EtOAc (20 ml), and the organic layer separated and combined with further EtOAc portions (2×10 ml). The extract was washed with brine (15 ml), dried (MgSO4), and concentrated in vacuo to give a pale brown oil. The residue was subjected to chromatography (SiO$_2$; EtOAc-hexane, 1:1) to afford the title compound (410 mg) as a colourless oil. δH (CDCl$_3$) 1.5–2.0 (8H, br m, (CH$_2$)$_4$), 3.86 and 3.89 (3H, s, OMe), 4.57 and 4.70 (1H, br m, OCH), 6.6–7.8 (14H, m, 2×C$_6$H$_4$ +C$_6$H$_3$+pyridine H$_3$, H$_5$+C=CH), and 8.3–8.45 (2H, m, pyridine H$_2$, H$_6$).

The following compound was prepared in a similar manner to the compound of Example 1a).

b) (E) and (Z) isomers of 4-[2-(3-Cyclopentyloxy-4-methoxy-phenyl)-2-(4'-methyl-4-biphenyl)ethenyl]pyridine From Intermediate 5 (0.40 g, 0.89 mmol), tetrakis (triphenylphosphine) palladium (0.051 g, 0.045 mmol) in DME (20 ml), sodium carbonate solution (2M, 1.49 ml, 2.7 mmol) and 4-methylbenzeneboronic acid (0.1151 g, 0.846 mmol). Chromatography (SiO$_2$; EtOAc-hexane, 1:1) afforded the title compound (0.311 g). δH (CDCl$_3$) 1.25 (1H, t), 1.5–1.75 (6H, m), 1.85 (2H, s), 2.4 (3H, s), 3.95 (3H, s), 6.4–6.9 (5H, m), 7.2–7.3 (3H, m), 7.5 (1H, m), 7.55–7.6 (3H, m), and 8.4 (2H, m).

EXAMPLE 2 a) (±)-4-{2-(3-Cyclopentyloxy-4-methoxyphenyl)-2-[4-(4trifluoromethyl phenyl)phenylethyl]}pyridinium formate A mixture of the compound of Example 1 (380mg) and 10% Pd/C (50 mg) in formic acid (5ml) and EtOH (35 ml) was heated to reflux for 3 h. The reaction mixture was filtered through Celite® and concentrated in vacuo to give a yellow oil which was subjected to chromatography (SiO$_2$; EtOAc-hexane, 1:1) to afford the title compound (190 mg) as a pale yellow solid. δH (CDCl$_3$) 1.5–1.95 (8H, br m, (CH$_2$)$_4$), 3.57 (2H, d, J 7.9 Hz, CHCH$_2$), 3.80 (3H, s, OMe), 4.24 (1H, t, J 7.9 Hz, CHCH$_2$), 4.68 (1H, br m, OCH), 6.65–6.75 (2H, m, 2×ArH meta to OMe), 6.78 (1H, d, J 8.1 Hz, ArH ortho to OMe), 7.29 (2H, d, J 8.2 Hz, 2×ArH meta to CF$_3$), 7.41 (2H, d, J 5.6 Hz, pyridine H$_3$,H$_5$), 7.53 (2H, d, 2×ArH ortho to CF$_3$), 7.63 (2H, d, J 8.8 Hz, 2×ArH of C$_6$H$_4$CF$_3$), 7.67 (2H, d, J 8.8 Hz, 2×ArH of C$_6$H$_4$CF$_3$), and 8.62 (2H, br d, J ca 5 Hz, pyridine H$_2$, H$_6$); mLz (EI) 517 (M$^+$, 8%), 426 (15), 425 (48), 358 (20), 357 (100), 296 (22), and 69 (28).

The following compound was prepared in a manner similar to the compound of Example 2a).

b) (±)-4-[2-(3-Cyclopentyloxy-4-methoxyphenyl)-2-(4'-methyl-4-biphenyl)ethyl]pyridine From the compound of Example 1b) (0.31 1 g, 0.673 mmol) in 10% formic acid in EtOH (35 ml) and 10% Pd/C. Purification by HPLC (60–80% acetonitrile-water) afforded the title compound (0.23 g). δH (MeOH) 1.5–1.75 (9H, m), 2.3 (3H, s), 3.3 (2H, dd), 3.5 (2H, d), 3.65 (3H, s), 4.3 (1H, t), 6.8 (3H, d), 7.2 (2H, d), 7.3 (2H, d), 7.35 (2H, d), 7.45 (2H, d), and 8.5 (2H, m). m/z (ES$^+$) 464.2 (M+H$^+$).

EXAMPLE 3

(R):4-[2-(4-Benzyloxyphenyl)-2-(3-cyclopentyloxy-4-methoxyphenyl)-ethyl]pyridine n-BuLi (1.6M solution in hexane) (27 ml, 43.0 mmol, 1.5 equiv) was added dropwise to a solution of ethanethiol (10.6 ml, 14.3 mmol, 5 equiv) in THF (300 ml) at ca −10° C. After 0.5 h, a solution of Intermediate 7 (20.6 g, 28.7 mmol) in THF (200 ml) was added dropwise and the reaction mixture allowed to stir at RT for 12.5 h. Water (10 ml) was added and the solvent removed in vacuo. The residual foam was dissolved in EtOH (100 ml) and aqueous sodium hydroxide (2M; 200 ml) and the mixture heated to reflux for 1 h. The reaction mixture was cooled to ca 50° C. and treated with concentrated hydrochloric acid (37 ml) to pH 5 then heated to reflux for 0.75 h. The organic solvents were removed in vacuo and the residue partitioned between aqueous NaOH solution (1.0M; 400 ml) and Et$_2$O (400 ml). The organic layer was separated, combined with further Et$_2$O volumes (3×100 ml), and the extract washed with aqueous NaOH solution (1.0M; 2×100 ml), then dried (MgSO$_4$), and concentrated in vacuo. The residual pale yellow gum was subjected to chromatography (SiO$_2$; hexane-Et$_2$O, 7:3 to 100% Et$_2$O) to afford the title compound (9.35 g) as a white solid (Found: C, 79.76; H, 6.98; N, 2.62. C$_{32}$H$_{33}$NO$_3$ requires C, 79.63; H, 7.11; N, 3.00%); δH (CDCl$_3$) 1.5,2.1 (8H, br m, (CH$_2$)$_4$), 3.27 (2H, d, J 7.8 Hz, CHCH$_2$), 3.79 (3H, s, OMe), 4.09 (1H, t, J 7.8 Hz, CHCH$_2$), 4.63 (1H, br m, OCH), 5.02 (2H, s, OCH$_2$), 6.64 (1H, d, J 2.0 Hz, ArH ortho to cyclopentyloxy), 6.67 (1H, dd, J 8.2, 2.0 Hz, ArH para to cyclopentyloxy), 6.74 (1H, d, J 8.2 Hz, ArH ortho to OMe), 6.87 (2H, ca. d, J ca. 8.6 Hz, 2×ArH ortho to benzyloxy), 6.91 (2H, ca d, J ca 4.5 Hz, pyridine H$_3$, H$_5$), 7.08 (2H, ca. d J ca. 8.6 Hz, 2×ArH meta to benzyloxy), 7.3–7.5 (5H, m, C$_6$H$_5$), and 8.38 (2H, dd, J 4.5,1.5 Hz, pyridine H$_2$, H$_6$).

EXAMPLE 4

(R)4-{2-(3-Cyclopentyloxy-4-methoxyphenyl)-2-[4-(4-nitrophenyloxy) phenyl]ethyl}pyridine Potassium tert.-butoxide (258mg, 2.19 mmol) was added to a solution of Intermediate 8 (710 mg, 1.83 mmol) in DMF (25 ml) and DMPU (10 ml) and the mixture stirred at RT. After 0.5 h, 4-bromonitrobenzene (553 mg, 2.74 mmol) was added and the solution stirred overnight at RT. Water (100 ml) and aqueous sodium hydroxide solution (2M, 20 ml) was added and the mixture extracted with Et$_2$O (3×150 ml). The extract was washed with aqueous sodium hydroxide solution (1M; 2×30 ml), water (2×100 ml), and brine (100 ml), then dried (MgSO$_4$), and concentrated in vacuo. The yellow residue was subjected to chromatography (SiO$_2$; Et$_2$O) to afford the title compound (729mg) as a pale yellow solid; δH (CDCl$_3$) 1.5–1.9 (8H, br m, (CH$_2$)$_4$), 3.32 (2H, d, J 7.9 Hz, CHCH$_2$), 3.81 (3H, s, OMe), 4.18 (1H, t, J 7.9 Hz, CHCH$_2$), 4.67 (1H, br m, OCH), 6.66 (1H, d, J 2.0 Hz, ArH ortho to cyclopentyloxy), 6.71 (1H, dd, J 8.2, 2.0 Hz, ArH para to cyclopentyloxy), 6.77 (1H, d, J 8.2 Hz, ArH ortho to OMe), 6.9–7.05 (6H, m, CHC$_6$H$_4$+pyridine H$_3$, H$_5$), 7.2–7.3 (2H, m, ArH meta to NO$_2$), 8.15–8.25 (2H, m, ArH ortho to NO$_2$), and 8.42 (2H, dd, J 4.5, 1.6 Hz, pyridine H$_2$, H$_6$).

EXAMPLE 5

(E) and (Z) isomers; of 4-[2-(3-Cyclopentyloxy-4-methoxyphenyl)-ethenyl]-3-(phenylethyl)pyridine A catalytic amount of tosic acid was added to a solution of compound of Example 10a) (1.8 g, 4.32 mmol) in toluene (150 ml) and the mixture heated to reflux in a Dean Stark equipment for 8 h. The reaction was cooled, poured into aqueous NaHCO$_3$ solution and extracted twice with CH$_2$Cl$_2$. The combined organic phase was dried (MgSO$_4$), filtered then concentrated in vacua. The residue was subjected to chromatography to give the title compound (1.3 g) as a yellow solid. m.p. 78°–80° C. (Found C, 81.44; H, 7.35; N, 3.62. C$_{27}$H$_{29}$NO$_2$ requires C, 81.17; H, 7.32; N, 3.51%). δH (CDCl$_3$) 1.6–2.0 (8H, br m, (CH$_2$)$_4$), 2.9–3.1 (4H, m, Ar(CH$_2$)$_2$), 3.81 (3H, s, OCH$_3$), 4.85 (1H, s, OCH), 6.9–7.4 (9H, m, ArH and CH=CH), 7.37 (1H, d, J 8 Hz, ArH), 8.37 (1H, s, H$_2$ pyridine) and 8.42 (1H, d, J 5 Hz, H$_6$pyridine).

EXAMPLE 6

4-[2-(3-Cyclopentyloxy-4-methoxyphenyl)ethyl]-3-(phenylethyl) pyridine.

The compound of Example 5 (800 m,g, 2 mmol) was hydrogenated using the reagents and conditions described for obtaining Intermediate 11 from Intermediate 10. Purification by chromatography (Si$_2$O; Et$_2$O) gave the title compound (605mg) as a colourless gum. (Found C, 80.82; H, 7.77; N, 3.54. C$_{27}$H$_{31}$NO$_2$ requires C, 80.76; H, 7.78; N, 3.49%). δH (CDCl$_3$) 1.5–1.9 (8H, m, (CH$_9$)$_4$), 3.27–3.29 (8H, m, alkyl H), 3.81 (3H, s, OCH$_3$), 4.67 (1H, m, OCH), 6.59 (1H, br s, ArH), 6.65 (1H, d, J 7 Hz, ArH), 6.78 (1H, d, J 7 Hz, ArH), 7.03 (1H, d, J 5 Hz, Hz pyridine), 7.1–7.4 (5H, m, C$_6$H$_5$), and 8.3–8.4 (2H, m, H$_2$, H$_6$ pyridine).

EXAMPLE 7

4-{2-(S)-[4-(4-Aminophenyloxy)phenyl]-2-(3-cyclopentyloxy-4-methoxyphenyl)ethyl]pyridine dihydrochloride A stirred solution of the compound of Example 4 (800 mg, 1.46 mmol) in EtOH (100 ml) was hydrogenated with 10% Pd/C (100 mg) under a hydrogen atmosphere for 24 h at RT. The reaction mixture was filtered through Celite® and the filtrate concentrated in vacuo to afford a yellow brown glass which was partitioned between aqueous 1 M NaOH and EtOAc. The combined organic phase was dried ($Na_2SO_4$) then concentrated in vacua to give an oily solid. Chromatography ($SiO_2$; EtOAc-$Et_2O$, 1:1) afforded the title compound free base (384.9 mg) as a near white solid. ιH ($CDCl_3$) 1.50–1.90 (8H, br m), 3.27 (2H, d, J 7.9 Hz), 3.79 (3H, s), 4.10 (1H, t, J 7.9 Hz), 4.65 (1H, br m), 6.63–6.69 (4M, m), 6.75 (1H, d, J 8.2 Hz), 6.80–6.85 (4H, m), 6.93 (2H, dd, J 4.5, 1.5 Hz), 7.09 (2H, dd, J 6.5, 2.0 Hz), and 8.38 (2H, dd, J 7.4, 1.5 Hz).

The free base (384.9 mg, 0.801 mmol) in $Et_2O$ (50 ml) was treated with 1.0M HCl in $Et_2O$ (1.76 ml) at RT. The resulting oily precipitate was dissolved by the addition of EtOH and the solvent removed in vacuo. The residue was suspended in $Et_2O$ and the solvent removed in vacuo to give a very pale buff solid. Recrystallisation (THF-EtOH) afforded the title compound as a very pale buff highly hygroscopic solid. δH ($CD_3OD$) 1.5–1.9 (8H, m), 3.72 (2H, m (overlap)), 3.76 (3H, s), 4.46 (1H, t, J 8.2 Hz), 4.75 (1H, m), 6.81 (1H, s), 6.84 (1H, s), 6.85 (1H, s), 6.97 (2H, dd, J 6.6, 2.0 Hz), 7.06 (2H, dd, J 6.75, 2.3 Hz), 7.30–7.40 (4H, m), 7.87 (2H, d, J 6.6 Hz) and 8.634 (2H, d, J 6.45 Hz). m/z ($EI^+$) 480 ($M^+$).

EXAMPLE 8 a) 4 {2-(S)-[4-(4-Acetamidophenyloxy]phenyl]-2-(3-cyclopentyl-oxy4methoxyphenyl)ethyl}pyridine hydrochloride A solution of the free base of compound of Example 7 (322 mg, 0.67 mmol) in pyridine (10 ml) was heated with acetic anhydride (126μl) and the mixture stirred at RT for 24 h. The solvent was removed in vacuo, the residue azeotroped twice with toluene and partitioned between aqueous NaOH (pH 13) and EtOAc. The aqueous layer was further extracted with EtOAc and the combined organic layer dried ($Na_2SO_4$) then concentrated in vacuo to give an off-white glass. Chromatography ($SiO_2$; EtOAc) afforded the title compound free base (303.6 mg) as an off-white glass.

Treatment of the free base (303.6 mg) in EtOH-$Et_2O$ (30 ml; 1:2) with 1.0M HCl in $Et_2O$ (0.62 ml) as described for the compound of Example 7 followed by the recrystallisation (THF-$Et_2O$) afforded the title compound as an off-white amorphous solid (highly hygroscopic). δH ($CD_3OD$) 1.50–1.90 (8H, br m), 2.11 (3H, s), 3.67 (2H, d, J 8.3 Hz), 3.76 (3H, s), 4.40 (1H, t, J 8.3 Hz), 4.73 (1H, br m), 6.79 (1H, s), 6.83 (1H, s), 6.84 (1H, s), 6.85–6.95 (4H, m), 7.28 (2H, d, (fine split), J 8.5 Hz), 7.50 (2H, dd, J 6.9, 2.3 Hz), 7.80 (2H, d, J 6.4 Hz), and 8.60 (2H, d, J 5.9 Hz).

The following compound was prepared in a manner similar to compound of Example 8a).

b) 4-{2-(S)-(3-Cyclopentyloxy-4-methoxyphenyl)-2-[4-(4-N',N'-dimethylaminosulphonylaminophenyl)phenyloxy] ethyl}pyridyl hydrochloride From the compound of Example 7 (250 mg, 0.52 mmol) in pyridine (15 ml) and dimethylsulphamoyl chloride (112μl, 1.04 mmol). Chromatography ($SiO_2$; EtOAc-$Et_2O$, 1:2) afforded the title compound free base (188.1 mg) as an off-white glass. δH ($CDCl_3$) 1.50–1.90 (8H, br m), 2.84 (6H, s), 3.29 (2H, t, J 7.9 Hz), 3.80 (3H, s), 4.13 (1H, t, J 7.9 Hz), 4.66 (1H, br m), 6.68 (1H, dd, J 8.2, 2.0 Hz), 6.76 (1H, d, J 8.2 Hz), 6.80–6.95 (6H, m), 7.14 (2H, d, J 8.6 Hz), 7.16 (2H, d, J 8.9 Hz), and 8.40 (2H, d, J 6.0Hz).

Treatment of the free base (259.1 mg, 0.44 mmol) in EtOH-$Et_2O$(40 ml, 1:1) with aqueous 1.0M HCl in $Et_2O$ (0.5 ml) followed by recrystallisation (THF-$Et_2O$) afforded the title compound as an highly hygroscopic off-white solid. m/z ($ES^+$) $M^+$+H 558. δH ($CD_3OD$) 1.50–1.90 (8H, br m), 2.77 (6H, s), 3.38 (2H, d, J 8.1 Hz), 3.76 (3H, s), 4.26 (1H, t, J 8.1Hz), 4.70 (1H, m), 6.74 (1H, d, J 1.9 Hz), 6.75–6.89 (6H, m), 7.10–7.30 (6H, m), and 8.29 (2H, dd, J 6,1.5 Hz).

EXAMPLE 9

4{2(S)-(3-Cyclopentyloxy-4-methoxyphenyl)-2-[4-(4-methylsulphonyl-aminophenyl)phenyloxy]ethyl}pyridine hydrochloride A solution of the free base of compound of Example 7 (0.3667 g, 0.6 mmol) and N-methylmorpholine (264μl, 0.24 mmol) in anhydrous $CH_2Cl_2$ (15 ml) was heated with metanesulphonylchloride (93μl, 1.2 mmol) and the mixture stirred at RT for 24 h. The crude mixture was partitioned between water and EtOAc and the aqueous layer further extracted with EtOAc. The combined organic layer was washed with aqueous 0.5M NaOH and brine, dried ($Na_2SO_4$) then concentrated in vacuo to give a pale brown glass. Chromatography ($SiO_2$; EtOAc-$Et_2O$, 2:1) afforded the title compound free base (230 mg) as an off-white glassy solid. δH ($CDCl_3$) 1.50–1.90 (8H, br m), 2.98 (3H, s), 3.29 (2H, d, J 7.9 Hz), 3.80 (3H, s), 4.14 (1H, t, J 7.9 Hz), 4.68 (1H, m), 6.65 (1H, d, J 2.0 Hz), 6.68 (1H, dd, J 8.2, 2.0 Hz), 6.77 (1H, d, J 8.2 Hz), 6.8–7.0 (6H, m), 7.15 (2H, d, J 8.6 Hz), 7.20 (2H, d, J 8.9 Hz), and 8.40 (2H, d, J 4.5, 1.5 Hz).

The salt was obtained using the procedure described for the compound of Example 7. From a solution of the free base (224.8 mg, 0.4024 mmol) in $Et_2O$-EtOH (40 ml, 3:1) and aqueous 1.0M HCl in $Et_2O$ (0.44 ml). Chromatography ($SiO_2$; $CH_2Cl_2$–5% MeOH) afforded a colourless glass which was recrystallised (THF-$Et_2O$) to give the title compound as a very hygroscopic off-white solid. m/z ($EI^+$) 550 ($M^+$).

EXAMPLE 10 a) (±) 4-[2-(3-Cyclopentyloxy-4-methoxyphenyl)-2-hydroxyethyl]-3-phenylethylpyridine n-BuLi (1.6M in hexanes) (8.03 mmol, 5.02 ml) was added dropwise to a solution of Intermediate 11 (1.45 g, 7.3 mmol) in THF and the mixture stirred for 30 min before adding a solution of Intermediate 12 (1.77 g, 8.03 mmol) in THF. The mixture was stirred for 30 min at −78° C., allowed to warm to RT, poured into aqueous $NaHCO_3$ solution, extracted twice with $CH_2Cl_2$, dried ($MgSO_4$), filtered and concentrated in vacuo. The residue was subjected to chromatography ($SiO_2$;EtOAc) to give the title compound (2.3 g) as an off-white solid.

The following compound was prepared in a manner similar to compound of Example 10 a).

b) [2-(3-Cyclolpentyloxy-pyrid-4-yl)-1-pyrid-4-yl] ethanol

From Intermediate 14 (1 g, 5.61 mmol) in THF (10 ml) under $N_2$, n-BuLi (1.6M) (3.5 ml) pyridine-4-carboxaldehyde (534 μl, 5.61 mmol). Chromatography ($SiO_2$; $Et_2O$) afforded the title compound (550 mg) as a yellow oil. δH ($CDCl_3$) 1.5–2.0 (8H, m, $(CH_2)_4$), 2.9 (2H, m, $CH_2$—CHOH), 4.93 (1H, t, CHOH), 5.37 (1H, m, OCH), 6.51 (1H, s, pyridine H'$_3$), 6.65 (1H, d, pyridine H'$_5$), 7.24 (2H, d, pyridine H$_3$, H$_5$), 8.2 (1H, d, pyridine H'$_5$), and 8.51 (2H, d, pyridine H$_2$, H$_6$).

The activity and selectivity of compounds according to the invention was demonstrated in the following tests. In these tests the abbreviation FMLP represents the peptide N-formyl-met-leu-phe.

1. Isolated Enzyme

The potency and selectivity of the compounds of the invention was determined using distinct PDE isoenzymes as follows:

i. PDE I, rabbit heart
ii. PDE II, rabbit heart
iii. PDE III, rabbit heart, Jurkat cells
iv. PDE IV, HL60 cells, rabbit brain, rabbit kidney and human recombinant PDE IV
V. PDE V, rabbit lung, guinea pig lung A gene encoding human PDE IV has been cloned from human monocytes (Livi, et al., 1990, *Molecular and Cellular Biology*, 10, 2678). Using similar procedures we have cloned human PDE IV genes from a number of sources including eosinophils, neutrophils, lymphocytes, monocytes, brain and neuronal tissues. These genes have been transfected into yeast using an inducible vector and various recombinant proteins have been expressed which have the biochemical characteristics of PDE IV (Beavo and Reifsnyder, 1990, TIPS, 11, 150). These recombinant enzymes, particularly the human eosinophil recombinant PDE IV, have been used as the basis of a screen for potent, selective PDE IV inhibitors.

The enzymes were purified to isoenzyme homogeneity using standard chromatographic techniques.

Phosphodiesterase activity was assayed as follows. The reaction was conducted in 150 μl of standard mixture containing (final concentrations): 50mM 2-[[tris (hydroxymethyl)methyl]amino]-1-ethanesulphonic acid (TES) —NaOH buffer (pH 7.5), 10 mM $MgCl_2$, 0.1μM [$^3$H]-cAMP and vehicle or various concentrations of the test compounds. The reaction was initiated by addition of enzyme and conducted at 30° C. for between 5 to 30 min. The reaction was terminated by addition of 50μl 2% trifluoroacetic acid containing [$^{14}$C]-5'AMP for determining recovery of the product. An aliquot of the sample was then applied to a column of neutral alumina and the [$^3$H]-cAMP eluted with 10 ml 0.1 TES—NaOH buffer (pH8). The [$^3$H]-5'-AMP product was eluted with 2 ml 2M NaOH into a scintillation vial containing 10 ml of scintillation cocktail. Recovery of [$^3$H]-5'AMP was determined using the [$^{14}$C]-5'AMP and all assays were conducted in the linear range of the reaction.

Compounds according to the invention such as compounds of the Examples herein cause a concentration-dependent inhibition of recombinant PDE IV at 0.1–1000 nM with little or no activity against PDE I, II, III or V at concentrations up to 100 μM.

2. The Elevation of cAMP in Leukocytes

The effect of compounds of the invention on intracellular cAMP was investigated using human neutrophils or guinea pig eosinophils. Human neutrophils were separated from peripheral blood, incubated with dihydrocytochalasin B and the test compound for 10 min and then stimulated with FMLP. Guinea pig eosinophils were harvested by peritoneal lavage of animals previously treated with intraperitoneal injections of human serum. Eosinophils were separated from the peritoneal exudate and incubated with isoprenaline and test compound. With both cell types, suspensions were centrifuged at the end of the incubation, the cell pellets were resuspended in buffer and boiled for 10 min prior to measurement of cAMP by specific radioimmunoassay (DuPont).

The most potent compounds according to the Examples induced a concentration -dependent elevation of cAMP in neutrophils and/or eosinophils at concentrations of 0.1 nM to 1 μM.

3. Suppression of Leukocyte Function

Compounds of the invention were investigated for their effects on superoxide generation, chemotaxis and adhesion of neutrophils and eosinophils. Isolated leukocytes were incubated with dihydrocytochalasin B for superoxide generation only and test compound prior to stimulation with FMLP. The most potent compounds of the Examples caused a concentration-dependent inhibition of superoxide generation, chemotaxis and adhesion at concentrations of 0.1 nM to 1μM.

Lipopolysaccharide (LPS)-induced synthesis of tumour necrosis factor (TNF) by human peripheral blood monocytes (PBM) is inhibited by compounds of the Examples at concentrations of 0.01 nM to 10μM.

4. Adverse Effects

In general, in our tests, compounds of the invention have had no observed toxic effects when administered to animals at pharmacologically effect doses.

We claim:

1. A compound of formula (1)

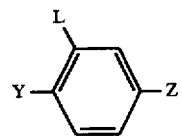

(1)

wherein

L is —XR, —C($R^{11}$)=C($R^1$)($R^2$) or —(CHR$^{11}$)$_n$CH ($R^1$) ($R^2$), where n is zero or an integer 1;

Z is a group (A) or (B):

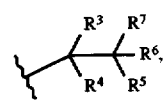

(A)

or

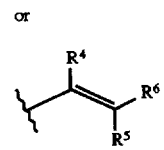

(B)

Y is halogen or an alkyl or —XR$^a$ group;

X is —O—, —S(O)$_m$— or —N(R$^b$)—, where m is zero or an integer 1 or 2;

each of R$^a$ and R$^b$ is independently hydrogen or an optionally substituted alkyl group;

R is an optionally substituted alkyl, alkenyl, cycloalkyl or cycloalkenyl group;

each of R$^1$ and R$^2$, which may be the same or different, is hydrogen, fluorine, —CN, —NO$_2$, or an optionally substituted alkyl, alkenyl, alkynyl, alkoxy, alkylthio, —CO$_2$R$^8$, —CNR$^9$R$^{10}$ or —CSNR$^9$R$^{10}$ group, or R$^1$ and R$^2$, together with the carbon atom to which thy are attached, are linked to form an optionally substituted cycloalkyl or cycloalkenyl group;

R$^3$ is hydrogen, fluorine, hydroxy or an optionally substituted straight or branched alkyl group;

R$^4$ is hydrogen, —(CH$_2$)$_t$Ar or —(CH$_2$)$_t$—Ar—(L$^1$)$_n$— Ar', where t is zero or an integer 1, 2 or 3;

$R^5$ is —(CH$_2$)$_x$Ar or —(CH$^2$)$_r$—Ar—(L$^1$)$_n$—Ar';

$R^6$ is hydrogen, fluorine, or an optionally substituted group;

$R^7$ is hydrogen, fluorine, an optionally substituted straight or branched alkyl group, or —OR$^c$, where R$^c$ is hydrogen, formyl, alkoxyalkyl, alkanoyl, carboxamido, thiocarboxamido or an optionally substituted alkyl or alkenyl group;

each of $R^8$, $R^9$ and $R^{10}$ is independently hydrogen or an optionally substituted alkyl, aralkyl or aryl group;

$R^{11}$ is hydrogen, fluorine or a methyl group;

$L^1$ is a divalent linking group;

Ar is a monocyclic or bicyclic aryl group, optionally containing one or more heteroatoms selected from oxygen, sulphur and nitrogen atoms;

Ar' is Ar, —COAr, —SO$_2$Ar, —SO$_2$NHAr, —SO$_2$NAlk$^1$Ar, —SO$_2$N(Ar)$_2$, —CONHAr, —CONAlk$^1$Ar, —CON(Ar)$_2$, —NAlk$^1$SO$_2$Ar, —NHSO$_2$Ar, —N(SO$_2$Ar)$_2$, —NHSO$_2$NHAr, —NAlk$^1$SO$_2$NHAr, —NHSO$_2$NAlk$^1$Ar, —NAlk$^1$SO$_2$NAlk$^1$Ar, —NHSO$_2$N(Ar)$_2$, —NAlk$^1$SO$_2$N(Ar)$_2$, —NHCOAr, —NAlk$^1$COAr, —N(COAr)$_2$, —NHCONHAr, —NAlk$^1$CONHAr, —NHCONAlk$^1$Ar, —NAlk$^1$CONAlk$^1$Ar, —NHCO$_2$Ar, —NAlk$^1$CO$_2$Ar, —CSNHAr, —CSNAlk$^1$Ar, —CSNAlk$^1$Ar, —CSN(Ar)$_2$, —NHCSAr, —NAlk$^1$CSAr, —N(CSAr)$_2$, —NHCSNHAr, —NAlk$^1$CSNHAr, —NHCSNAlk$^1$Ar, —NAlk$^1$CSNAlk$^1$Ar, —SO$_2$NHet, —CONHet, —CSNHet, —NHSO$_2$NHet, —NHCONHet, —NHCSNHet, —SO$_2$NH(Het'), —CONH(Het'), —CSNH(Het'), —NHSO$_2$NH(Het'), —NHCONH(Het') or —NHCSNH(Het');

Alk$^1$ is a straight or branched C$_{1-6}$alkylene, C$_{2-6}$alkenylene or C$_{2-6}$alkynylene chain optionally interrupted by one, two or three —O— or —S— atoms or —S(O)$_p$— or —N(R$^b$)— groups, where p is an integer 1 or 2;

NHet is an optionally substituted C$_{5-7}$heterocyclic amino group optionally containing one or more additional —O— or —S— atoms or —N(R$^b$)—, —CO— or —CS— groups;

Het' is an optionally substituted C$_{5-7}$monocyclic carbocyclic group optionally containing one or more —O— or —S— atoms or —N(R$^b$)— groups; and the salts, solvate, hydrates, prodrugs and N-oxides thereof;

with the proviso that when R$^r$ is —(CH$_2$)$_r$Ar and L is —XR, then R$^4$ is —(CH$_2$)$_r$—Ar—(L$^1$)$_n$Ar'.

2. A compound according to claim 1 wherein [==W— is a =C(XR$^a$)—group and ] L is an —XR group.

3. A compound according to claim 2 wherein Z is a group (A), R$^3$, R$^6$ and R$^7$ is each a hydrogen atom, R$^4$ is a group —(CH$_2$)$_r$—Ar—(L$^1$)$_n$—Ar' and R$^5$ is a group —(CH$_2$)$_r$Ar.

4. A compound according to claim 3 wherein Ar in R$^4$ is an optionally substituted phenyl group and Ar in R$^5$ is an optionally substituted pyridyl group.

5. A compound according to claim 4 wherein R$^4$ is a group —Ar—Ar, —Ar—O—Ar, —Ar—CH$_2$—Ar, —Ar—(CH$_2$)$_2$Ar, —Ar—NHC(O)NHAr, —Ar—CH$_2$NHC(O)NHAr, —Ar—COAr, —Ar—CH$_2$COAr, —Ar—NHSO$_2$NHAr, —Ar—CH$_2$NHSO$_2$NHAr, —Ar—NHSO$_2$Ar, —Ar—CH$_2$NHSO$_2$Ar, —Ar—NCH$_3$C(O)NHAr, —Ar—CH$_2$NCH$_3$C(O)NHAr, —Ar—NCH$_3$SO$_2$NHAr or —Ar—CH$_2$NCH$_3$SO$_2$NHAr groups.

6. A compound according to claim 5 wherein R$^5$ is an optionally substituted pyridyl group.

7. A compound according to claim 2 wherein Z is a group B, R$^4$ and R$^6$ is each a hydrogen atom and R$^5$ is a —(CH$_2$)$_r$—Ar—(L$^1$)$_n$—Ar' group.

8. A compound according to claim 7 wherein R$^5$ is an —Ar—(L$^1$)$_n$Ar' group.

9. A compound which is:

(±)-4-{2-(3-Cyclopentyloxy-4-methoxyphenyl)-2-[4-(4-trifluoromethyl-phenyl) phenylethyl]}pyridine;

(±)-4-[2-(4-Benzyloxyphenyl)-2-(3-cyclopentyloxy-4-methoxyphenyl)-ethyl]pyridine;

(±)-4-{2-(3-Cyclopentyloxy-4-methoxyphenyl)-2-[4-(4-nitrophenyloxy)-phenyl]ethyl}pyridine; (E) and (Z) isomers of 4-[2-(3-Cyclopentyloxy-4-methoxyphenyl)-ethenyl]-3-(phenylethyl)pyridine);

(±)-4-[2-(3-Cyclopentyloxy-4-methoxyphenyl)ethyl]-3-(phenylethyl)-pyridine;

(±)-4-{2-[4-(4-Aminophenyloxy)phenyl]-2-(3-cyclopentyloxy-4-methoxyphenyl)ethyl}pyridine;

(±)-4-{2-[4-(4-Acetamidophenyloxy)phenyl]-2-(3-cyclopentyloxy-4-methoxyphenyl)ethyl]pyridine;

(±)-4-{2-(3-Cyclopentyloxy-4-methoxyphenyl)-2-[4-(4—N',N'-dimethyl-aminosulphonylaminophenyl) phenyloxy]ethyl}pyridine;

(±)-4-{2-(3-Cyclopentyloxy-4-methoxyphenyl)-2-[4-(4-methyl-sulphonylaminophenyl)phenyloxy]ethyl}pyridine;

(±)-4-[2-(3-Cyclopentyloxy-4-methoxyphenyl)-2-(4'-methyl-4-biphenyl)-ethyl]pyridine;

(±)—N-{3-[1-(3-Cyclopentyloxy-4-methoxyphenyl)-2-(4-pyridyl)ethyl]-phenyl-methyl}-N'phenylurea;

or each isomer or the resolved enantioners, and the salts, solvates, hydrates, prodrugs and N-oxides thereof.

10. A compound according to claim 9 which is (±)-4-[2-(4-benzyloxyphenyl)-2-(3-cyclopentyloxy-4-methoxyphenyl)ethyl]pyridine; or a salt, solvate, hydrate or N-oxide thereof.

11. A compound according to claim 9 which is (R)-4-[2-(4-benzyloxyphenyl)-2-(3-cyclopentyloxy-4-methoxyphenyl)ethyl]pyridine; or a salt, solvate, hydrate or N-oxide thereof.

12. A pharmaceutical composition comprising, in combination with one or more pharmaceutically acceptable carriers, excipients or diluents, (±)-4-[2-(4-benzyloxyphenyl)-2-(3-cyclopentyloxy-4-methoxyphenyl) ethyl]pyridine or a resolved enantiomer thereof, or a salt, solvate, hydrate or N-oxide thereof.

13. A composition according to claim 12 which comprises (R)-4-[2-(4-benzyloxyphenyl)-2-(3-cyclopentyloxy-4-methoxyphenyl)ethyl]pyridine or a salt, solvate, hydrate or N-oxide thereof.

14. A method of preventing or treating an inflammatory disease in a patient comprising administering to the patient, in an amount effective to elevate intracellular levels of adenosine 3', 5'-cyclic monophosphate (cAMP), a composition which comprises a selective inhibitor of a phosphodiesterase (PDE) IV isoenzyme selected from a compound according to claim 1 and a pharmaceutically acceptable carrier, excipient or diluent.

15. A method according to claim 14 wherein said inflammatory disease is asthma.

16. A method according to claim 14 wherein said inflammatory disease is selected from the group consisting of inflammatory airway disease, chronic bronchitis, eosinophilic granuloma, cellular proliferative disorders, endotoxic shock, septic shock, ulcerative colitis, Crohn's disease, reperfusion injuries, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restenosis and artherosclerosis.

17. A compound of formula (2)

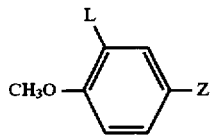
(2)

wherein

L is —OR, —CH=C(R$^1$)(R$^2$) or —CH$_2$CH(R$^1$)(R$^2$);

Z is a group (A) or (B):

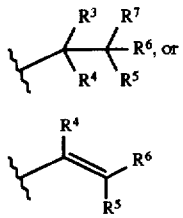
(A)

(B)

Y is halogen or an alkyl or —XR$^a$ group;

R is an optionally substituted cycloalkyl group;

R$^1$ and R$^2$, together with the carbon atom to which they are attached, are linked to form an optionally substituted cycloalkyl group;

R$^3$ is hydrogen, fluorine, hydroxy or an optionally substituted straight or branched alkyl group;

R$^4$ is hydrogen, —(CH$_2$)$_t$Ar or —(CH$_2$)$_t$—Ar—(L$^1$)$_n$—Ar', where n is zero or an integer 1 and t is zero or an integer 1, 2 or 3;

R$^5$ is —(CH$_2$)$_t$Ar or —(CH$_2$)$_t$Ar—(L$^1$)$_n$—Ar';

R$^6$ is hydrogen, fluorine, or an optionally substituted alkyl group;

R$^7$ is hydrogen, fluorine, an optionally substituted straight or branched alkyl group, or —OR$^c$, where R$^c$ is hydrogen, formyl, alkoxyalkyl, alkanoyl, carboxamido, thiocarboxamido or an optionally substituted alkyl or alkenyl group;

L$^1$ is a divalent linking group;

Ar is a monocyclic or bicyclic aryl group, optionally containing one or more heteroatoms selected from oxygen, sulphur and nitrogen atoms;

Ar' is Ar, —COAr, —SO$_2$Ar, —SO$_2$NHAr, —SO$_2$NAlk$^1$Ar, —SO$_2$N(Ar)$_2$, —CONHAr, —CONAlk$^1$Ar, —CON(Ar)$_2$, —NAlk$^1$SO$_2$Ar, —NHSO$_2$Ar, —N(SO$_2$Ar)$_2$, —NHSO$_2$NHAr, —NAlk$^1$SO$_2$NHAr, —NHSO$_2$NAlk$^1$Ar, —NAlk$^1$SO$_2$NAlk$^1$Ar, —NHSO$_2$N(Ar)$_2$, —NAlk$^1$SO$_2$N(Ar)$_2$, —NHCOAr, —NAlk$^1$COAr, —N(COAr)$_2$, —NHCONHAr, —NAlk$^1$CONHAr, —NHCONAlk$^1$Ar, —NAlk$^1$CONAlk$^1$Ar, —NHCO$_2$Ar, —NAlk$^1$CO$_2$Ar, —CSNHAr, —CSNAlk$^1$Ar, —CSNAlk$^1$Ar, —CSN(Ar)$_2$, —NHCSAr, —NAlk$^1$CSAr, —N(CSAr)$_2$, —NHCSNHAr, —NAlk$^1$CSNHAr, —NHCSNAlk$^1$Ar, —NAlk$^1$CSNAlk$^1$Ar, —SO$_2$NHet, —CONHet, —CSNHet, —NHSO$_2$NHet, —NHCONHet, —NHCSNHet, —SO$_2$NH(Het'), —CONH(Het'), —CSNH(Het'), —NHSO$_2$NH(Het'), —NHCONH(Het') or —NHCSNH(Het');

Alk$^1$ is a straight or branched C$_{1-6}$alkylene, C$_{2-6}$alkenylene or C$_{2-6}$alkynylene chain optionally interrupted by one, two or three —O— or —S— atoms or —S(O)$_p$— or —N(R$^b$)— groups, where p is an integer 1 or 2;

NHet is an optionally substituted C$_{5-7}$heterocyclic amino group optionally containing one or more additional —O— or —S— atoms or —N(R$^b$)—, —CO— or —CS— groups;

Het' is an optionally substituted C$_{5-7}$monocyclic carbocyclic group optionally containing one or more —O— or —S— atoms or N(R$^b$) groups; and the salts, solvates, hydrates, prodrugs and N-oxides thereof; with the proviso that when R$^5$ is —(CH$_2$)$_t$Ar and L is —XR, then R$^4$ is —(CH$_2$)$_t$—Ar—(L$^1$)$_n$Ar'.

18. A compound according to claim 17 wherein Z is group (A), R$^3$ is hydrogen, R$^6$ is hydrogen or methyl and R$^7$ is hydrogen or methyl.

19. A compound according to claim 18 wherein R$^6$ and R$^7$ are hydrogen.

20. A pharmaceutical composition comprising a compound of formula (1)

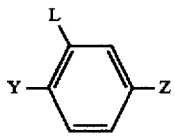
(1)

wherein

L is —XR, —C(R$^{11}$)=C(R$^1$)(R$^2$) or —(CHR$^{11}$)$_n$CH(R$^1$)(R$^2$), where n is zero or an integer 1;

Z is a group (A) or (B):

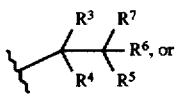
(A)

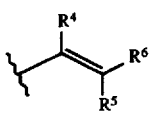
(B)

Y is halogen or an alkyl or —XR$^a$ group;

X is —O—, —S(O)$_m$— or —N(R$^b$)—, where m is zero or an integer 1 or 2;

each of R$^a$ and R$^b$ is independently hydrogen or an optionally substituted alkyl group;

R is an optionally substituted alkyl, alkenyl, cycloalkyl or cycloalkenyl group;

each of R$^1$ and R$^2$, which may be the same or different, is hydrogen, fluorine, —CN, —NO$_2$, or an optionally substituted alkyl, alkenyl, alkynyl, alkoxy, alkylthio, —CO$_2$R$^8$, —CNR$^9$R$^{10}$ or —CSNR$^9$R$^{10}$ group, or R$^1$ and R$^2$, together with the carbon atom to which they are attached, are linked to form m optionally substituted cycloalkyl or cycloalkenyl group;

R$^3$ is hydrogen, fluorine, hydroxy or an optionally substituted straight or branched alkyl group;

R$^4$ is hydrogen, —(CH$_2$)$_t$Ar or —(CH$_2$)$_t$—Ar—(L$^1$)$_n$—Ar', where t is zero or an integer 1, 2 or 3;

R$^5$ is —(CH$_2$)$_t$Ar or —(CH$_2$)$_t$—Ar—(L$^1$)$_n$—Ar';

R$^6$ is hydrogen, fluorine, or an optionally substituted alkyl group;

37

R⁷ is hydrogen, fluorine, an optionally substituted straight or branched alkyl group, or —OR^c, where R^c is hydrogen, formyl, alkoxyalkyl, alkanoyl, carboxamido, thiocarboxamido or an optionally substituted alkyl or alkenyl group;

each of R⁸ R⁹ and R¹⁰ is independently hydrogen or an optionally substituted alkyl, aralkyl or aryl group;

R¹¹ is hydrogen, fluorine or a methyl group;

L¹ is a divalent linking group;

Ar is a monocyclic or bicyclic aryl group, optionally containing one or more heteroatoms selected from oxygen, sulphur and nitrogen atoms;

Ar' is Ar, —COAr, —SO₂Ar, —SO₂NHAr, —SO₂NAlk¹Ar, —SO₂N(Ar)₂—CONHAr, —CONAlk¹Ar, —CON(Ar)₂, —NAlk¹SO₂Ar, —NHSO₂Ar, —N(SO₂Ar)₂, —NHSO₂NHAr, —NAlk¹SO₂NHAr, —NHSO₂NAlk¹Ar, —NAlk¹SO₂NAlk¹Ar, —NHSO₂N(Ar)₂, —NAlk¹SO₂N(Ar)₂, —NHCOAr, —NAlk¹COAr, —N(COAr)₂, —NHCONHAr, —NAlk¹CONHAr, —NHCONAlk¹Ar, —NAlk¹CONAlk¹Ar, —NHCO₂Ar, —NAlk¹CO₂Ar, —CSNHAr, —CSNAlk¹Ar, —CSNAlk¹Ar, —CSN(Ar)₂, —NHCSAr, —NAlk¹CSAr, —N(CSAr)₂, —NHCSNHAr, —NAlk¹CSNHAr, —NHCSNAlk¹Ar, —NAlk¹CSNAlk¹Ar, —SO₂NHet, —CONHet, —CSNHet, —NHSO₂NHet, —NHCONHet, —NHCSNHet —SO₂NH(Het'), —CONH(Het'), —CSNH(Het'), —NHSO₂ NH(Het'), —NHCONH (Het') or —NHCSNH(Het');

Alk¹ is a straight or branched C₁₋₆alkylene, C₂₋₆alkynylene or C₂₋₆alkynylene chain optionally interrupted by one, two or three —O— or —S— atoms or —S(O)_p— or —N(R^b)— groups, where p is an integer 1 or 2;

NHet is an optionally substituted C₅₋₇heterocyclic amino group optionally containing one or more additional —O— or —S— atoms or —N(R^b)—, —CO— or —CS— groups;

Het' Is an optionally substituted C₅₋₇monocyclic carbocyclic group optionally containing one or more —O— or —S— atoms or —N(R^b)— groups; and the salts, solvates, hydrates, prodrugs and N-oxides thereof; with the proviso that when R⁵ is —(CH₂)_tAr and L is —XR, then R⁴ is —(CH₂)_t—Ar—(L¹)_nAr';

together with one or more pharmaceutically acceptable carriers, excipients or diluents.

21. A process for the preparation of a compound of formula (1)

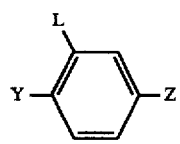

wherein

L is —XR, —C(R¹¹)=C(R¹)(R²) or —(CHR¹¹)_nCH(R¹) (R²), where n is zero or an integer 1;

38

Z is a group (A) or (B):

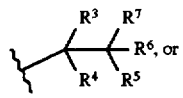

(A)

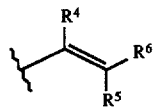

(B)

Y is halogen or an alkyl or —XR^a group,

X is —O—, —S(O)_m— or —N(R^b)—, where m is zero or an integer 1 or 2;

each of R^a and R^b is independently hydrogen or an optionally substituted alkyl group;

R is an optionally substituted alkyl, alkenyl, cycloalkyl or cycloalkenyl group;

each of R¹ and R², which may be the same or different, is hydrogen, fluorine, —CN,e —NO₂, or an optionally substituted alkyl, alkenyl, alkynyl, alkoxy, alkylthio, —CO₂R⁸, —CNR⁹R¹⁰ or —CSNR⁹R¹⁰ group, or R¹ and R², together with the carbon atom to which they are attached, are linked to form an optionally substituted cycloalkyl or cycloalkenyl group;

R³ is hydrogen, fluorine, hydroxy or anti optionally substituted straight or branched alkyl group;

R⁴ is hydrogen, —(CH₂)_tAr or —(CH₂)_t—Ar—(L¹)_n— Ar', where t is zero or an integer 1,2 or 3;

R⁵is —(CH₂)_tAr or —(CH₂)_t—Ar—(L¹)_n—Ar';

R⁶ is hydrogen, fluorine, or an optionally substituted alkyl group;

R⁷ is hydrogen, fluorine, an optionally substituted straight or branched alkyl group, or —OR^c, where R^c is hydrogen, formyl, alkoxyalkyl, alkanoyl, carboxamido, thiocarboxamido or an optionally substituted alkyl or alkenyl group;

each of R⁸, R⁹ and R¹⁰ is independently hydrogen or an optionally substituted alkyl, aralkyl or aryl group;

R¹¹ is hydrogen, fluorine or a methyl group;

L¹ is a divalent linking group;

Ar is a monocyclic or bicyclic aryl group, optionally containing one or more heteroatoms selected from oxygen, sulphur and nitrogen atoms;

Ar' is Ar, —COAr, —SO₂Ar, —SO₂NHAr, —SO₂NAlk¹Ar, —SO₂N(Ar)₂, —CONHAr, —CONAlk¹Ar, —CON(Ar)₂, —NAlk¹SO₂Ar, —NHSO₂Ar, —N(SO₂Ar)₂ , —NHSO₂NHAr, —NAlk¹SO₂NHAr, —NHSO₂NAlk¹Ar, —NAlk¹SO₂NAlk¹Ar, —NHSO₂N(Ar)₂, —NAlk¹SO₂N(Ar)₂, —NHCOAr, —NAlk¹COAr, —N(COAr)₂, —NHCONHAr, —NAlk¹CONHAr, —NHCONAlk¹Ar, —NAlk¹CONAlk¹Ar, —NHCO₂Ar, —NAlkA¹CO₂Ar, —CSNHAr, —CSNAlk¹Ar, —CSNAlk¹Ar, —CSN(Ar)₂, —NHCSAr, —NAlk¹CSAr, —N(CSAr)₂, —NHCSNHAr, —NAlk¹CSNHAr, —NHCSNAlk¹Ar, —NAlk¹CSNAlk¹Ar, —SO₂NHet, —CONHet, —CSNHet, —NHSO₂NHet, —NHCONHet, —NHCSNHet, —SO₂NH(Het'), —CONH(Het'), —CSNH(Het'), —NHSO₂NH(Het'), —NHCONH (Het') or —NHCSNH(Het');

Alk¹ is a straight or branched $C_{1-6}$alkylene, $C_{2-6}$alkenylene or $C_{2-6}$alkynylene chain optionally interrupted by one, two or three —O— or —S— atoms or $S(O)_p$— or —N(R^b) groups, where p is an integer 1 or 2;

NHet is an optionally substituted $C_{5-7}$heterocyclic amino group optionally containing one or more additional —O— or —S— atoms or —N(R^b)—, —CO— or —CS— groups;

Het' is an optionally substituted $C_{5-7}$monocyclic carbocyclic group optionally containing one or more —O— or —S— atoms or —N(R^b)— groups; and the salts, solvates, hydrates, prodrugs and N-oxides thereof, with the proviso that when R⁵ is —(CH₂)ᵣAr and L is —XR, then R⁴ is —(CH₂)ᵣ—Ar—(L¹)ₙAr':

(a) coupling a compound of formula (3)

(3)

with (i) an olefination agent to give a compound of formula (1), where L is —C(R¹¹)=C(R¹)(R²) in which R¹¹ is hydrogen or a methyl group; or (ii) an organometallic agent, followed by dehydration of the corresponding alcohol to give a compound of formula (1), where L is —C(R¹¹)=CH (R¹) in which R¹ is an optional substituted alkyl, alkenyl or alkynly group;

(b) reacting a compound of formula (10)

(10)

with a phosphate ester (R'O)(OR")P(O)CH(R⁵)(R⁶) to give a compound of formula (1), where Z is a group (B);

(c) coupling a compound of formula (12)

(12)

wherein (i) Z¹ is as defined for Z in formula (1) except that at least one of R⁴ and R⁵ is a group —(CH₂)ᵣArE, where E is a boronic acid —B(OH)₂ or a tin reagent Sn(R¹⁵)₃ in which R¹⁵ is an alkyl group;

with a reagent Ar'—(L¹)ₙ—L², wherein L² is a leaving group, in the presence of a complex metal catalyst to give a compound of formula (1) wherein at least one of R⁴ and R⁵ is a —(CH₂)ₙ—Ar—(L¹)ₙ—Ar' group; or (ii) Z¹ is as defined for Z in formula (1) except that at least one of R⁴ and R⁵ is a group —(CH₂)ᵣArXᵃH;

with a reagent Ar'(Alk⁵)ᵣL¹ to give a compound of formula (1) wherein at least one of R⁴ and R⁵ is a group —(CH₂)ᵣArL¹Ar' in which L¹ is —Xᵃ(Alk⁵)ᵣ—.

(d) reacting a compound of formula (13)

(13)

where Hal is a halogen atom, with a diazoalkane CH(R¹)N₂, followed by reaction with a regent R⁸OH or R⁹R¹⁰NH in the presence of silver oxide or a silver salt, optionally in the presence of a base, to give a compound of formula (1), where L is a group —CH(R¹)(R²) in which R² is CO₂R⁸ or —CONR⁹R¹⁰; or (e) interconverting a compound of formula (1) to give another compound of formula (1).

* * * * *